United States Patent
Balaconis et al.

(10) Patent No.: US 10,772,546 B2
(45) Date of Patent: Sep. 15, 2020

(54) MULTI-ANALYTE SENSING TISSUE-INTEGRATING SENSORS

(71) Applicant: Profusa, Inc., Emeryville, CA (US)

(72) Inventors: Mary K. Balaconis, College Station, TX (US); Scott Nichols, South San Francisco, CA (US); Sierra Guidry, Bryan, TX (US); Yu Zhang, College Station, TX (US); Ryan Schweller, College Station, TX (US); Soya Gamsey, San Francisco, CA (US); Jacob William Clary, Moss Beach, CA (US); Sulolit Pradhan, Foster City, CA (US); Natalie Wisniewski, San Francisco, CA (US)

(73) Assignee: Profusa, Inc., Emeryville, CA (US)

( * ) Notice: Subject to any disclaimer, the term of this patent is extended or adjusted under 35 U.S.C. 154(b) by 258 days.

(21) Appl. No.: 16/023,906

(22) Filed: Jun. 29, 2018

(65) Prior Publication Data

US 2019/0000364 A1  Jan. 3, 2019

Related U.S. Application Data

(60) Provisional application No. 62/526,961, filed on Jun. 29, 2017.

(51) Int. Cl.
*A61B 5/1455* (2006.01)
*G01N 33/58* (2006.01)
(Continued)

(52) U.S. Cl.
CPC ........ *A61B 5/14556* (2013.01); *A61B 5/1459* (2013.01); *A61B 5/14552* (2013.01);
(Continued)

(58) Field of Classification Search
CPC .............. A61B 5/1455; A61B 5/14532; A61B 5/14542; A61B 5/14546; A61B 5/14551;
(Continued)

(56) References Cited

U.S. PATENT DOCUMENTS 6,362,175 B1 * 3/2002 Vinogradov ....... A61B 5/14556
424/9.61
6,602,716 B1    8/2003 Klimant
(Continued)

OTHER PUBLICATIONS

International Search Report and Written Opinion dated Nov. 9, 2018, for International Application No. PCT/US2018/040455, 11 pages.

*Primary Examiner* — Eric F Winakur
(74) *Attorney, Agent, or Firm* — Cooley LLP

(57) ABSTRACT

Some embodiments described herein relate to a sensor that includes a first a first polymer-luminescent sensing compound configured to produce a first luminescent signal in the presence of a first analyte and a second polymer-luminescent sensing compound configured to produce a second luminescent signal in the presence of a second analyte. The second luminescent signal can have a luminescent lifetime that is at least 1.1 times greater than a luminescent lifetime of the first luminescent signal. Such temporally differences in signal can be used to deconvolute the first luminescent signal from the second luminescent signal even when, for example, the first luminescent signal and the second luminescent signal have the same or a similar emission spectrum.

18 Claims, 7 Drawing Sheets

(51) Int. Cl.
    *A61B 5/1459*     (2006.01)
    *A61B 5/145*     (2006.01)
    *A61B 5/00*     (2006.01)

(52) U.S. Cl.
    CPC ......... *A61B 5/0031* (2013.01); *A61B 5/14532* (2013.01); *A61B 5/14542* (2013.01); *G01N 33/582* (2013.01); *G01N 2333/904* (2013.01)

(58) Field of Classification Search
    CPC . A61B 5/14556; A61B 5/1459; A61B 5/6846; A61B 5/686; A61B 5/72; A61B 5/7271
    See application file for complete search history.

(56) References Cited

U.S. PATENT DOCUMENTS

| | | | |
|---|---|---|---|
| 9,375,494 B2 | 6/2016 | Gamsey et al. | |
| 9,517,023 B2 | 12/2016 | McMillan et al. | |
| 9,650,566 B2 | 5/2017 | Gamsey et al. | |
| 9,867,560 B2 | 1/2018 | Gamsey et al. | |
| 10,010,272 B2 | 7/2018 | Wisniewski et al. | |
| 10,045,722 B2 | 8/2018 | Kintz et al. | |
| 10,117,613 B2 | 11/2018 | Wisniewski et al. | |
| 10,219,729 B2 | 3/2019 | Kintz et al. | |
| 10,383,557 B2 | 8/2019 | Gamsey et al. | |
| 10,463,287 B2 | 11/2019 | Wisniewski et al. | |
| 10,494,385 B2 | 12/2019 | Gamsey et al. | |
| 10,583,308 B2 | 3/2020 | McMillan et al. | |
| 2002/0010279 A1* | 1/2002 | Satcher, Jr. ............ | G01N 33/52 525/255 |
| 2002/0043651 A1 | 4/2002 | Darrow et al. | |
| 2012/0265034 A1 | 10/2012 | Wisniewski et al. | |
| 2013/0060107 A1 | 3/2013 | Crane et al. | |
| 2014/0286875 A1 | 9/2014 | Gamsey et al. | |
| 2014/0364707 A1 | 12/2014 | Kintz et al. | |
| 2016/0374556 A1 | 12/2016 | Colvin, Jr. et al. | |
| 2018/0177443 A1 | 6/2018 | Rice et al. | |
| 2018/0179233 A1 | 6/2018 | Gamsey et al. | |
| 2018/0256108 A1 | 9/2018 | Au-Yeung et al. | |
| 2019/0029572 A1 | 1/2019 | Wisniewski et al. | |
| 2019/0192057 A1 | 6/2019 | Kintz et al. | |
| 2019/0200865 A1 | 7/2019 | Hwang et al. | |
| 2019/0352510 A1 | 11/2019 | Colvin | |
| 2020/0000383 A1 | 1/2020 | Gamsey et al. | |
| 2020/0000940 A1 | 1/2020 | Balaconis et al. | |
| 2020/0008716 A1 | 1/2020 | Kintz et al. | |
| 2020/0023079 A1 | 1/2020 | Balaconis et al. | |
| 2020/0107762 A1 | 4/2020 | Gamsey et al. | |

* cited by examiner

MULTI-ANALYTE SENSING TISSUE-INTEGRATING SENSORS

CROSS REFERENCE TO RELATED APPLICATIONS

This application claims priority to U.S. Provisional Application No. 62/526,961, filed on Jun. 29, 2017, the disclosures of each of which is hereby incorporated by reference in its entirety. This application is related to U.S. Patent Pub. No. 20120265034, entitled "Tissue-integrating sensors," published on Oct. 18, 2012; and U.S. Pat. No. 9,375,494, entitled "Oxygen sensors," issued on Jun. 28, 2016; the entire disclosures of which are incorporated herein by reference.

TECHNICAL FIELD

The presently disclosed subject matter relates generally to sensors for monitoring analyte levels in the body of a human or animal patient and/or subject. Sensors described herein generally include one or more polymers and one or more luminescent sensing compounds configured to emit a luminescent signal that is dependent on a concentration and/or quantity of an analyte. Some embodiments described herein include sensors and methods for detecting multiple analytes.

BACKGROUND

Currently, sensors exist that can be implanted and integrate into the tissue of human or animal patients and/or subjects. For example, sensors exist that can be implanted a few millimeters under the skin. For example, U.S. Patent Application Pub. No. 2012/0265034, entitled "Tissue-integrating sensors," published on Oct. 18, 2012 and U.S. Pat. No. 9,375,494, entitled "Oxygen sensors," issued on Jun. 28, 2016, the entire disclosures of which are incorporated herein by reference, describe various implantable tissue-integrating sensors. Typically, in such sensors, luminescent sensing compounds are used to measure the concentration of an analyte of interest (e.g., oxygen ($O_2$), glucose, lactate, or pyruvate). In addition to luminescent sensing compounds and other components, implantable sensors can include polymers or polymeric hydrogels.

A need exists for implantable sensors capable of detecting more than one analyte. It is difficult or impossible to detect more than one analyte using existing sensors. A particular challenge exists in deconvoluting signals associated with the different analytes detected by a sensor. Additionally, a polymer scaffold suitable for one luminescent sensing compound may not be suitable for a luminescent sensing compound configured to detect another analyte. Embodiments described herein relate to combinations of luminescent sensing compounds and polymerss particularly well suited to improve luminescent sensing compound performance and/or suitable for use as part of a multi-analyte sensing sensor.

DETAILED DESCRIPTION

Figure 1:
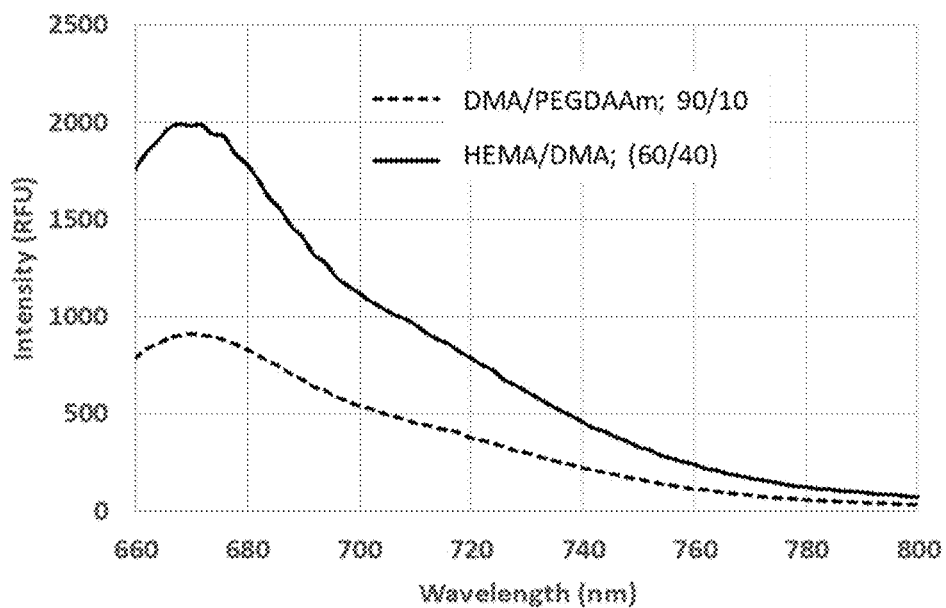
FIG. 1 is a chart illustrating a luminescent glucose sensitive compound having variable luminescent intensity depending on polymer matrix, according to an embodiment.

Some embodiments described herein relate to a sensor and an analyte detection system for detecting multiple analytes simultaneously. For example, an analyte detection system can include a multi-analyte sensor that includes polymers and luminescent sensing compounds. The multi-analyte sensor may be implanted in tissue (e.g., a few millimeters under the skin) of a human or animal patient and/or subject. An optical detector (or reader) that can be placed on the surface of the skin can be operable to detect signals emitted by the multi-analyte sensor. The multi-analyte detection system can further include processing capability (e.g., a computing entity) for processing any information from the optical detector.

Some embodiments described herein relate to combinations (or formulations) typically containing at least a polymer (e.g., a hydrogel) and a luminescent sensing compound (also referred to herein as a "dye"). For ease of description, a formulation containing a luminescent sensing compound and at least one polymer may be referred to herein as a dye-polymer composition or a polymer-luminescent sensing compound. The luminescent sensing compound is typically configured to emit a signal that can be correlated to a quantity or concentration of an analyte. In some instances, the luminescent sensing compound can be excited by a first optical signal and emit a second optical signal (e.g., via phosphorescence or fluorescence) that is dependent upon a quantity or concentration of the analyte. The polymer can make up or be a component of a tissue-integrating scaffold, which can contain the luminescent sensing compound, ensure that the luminescent sensing compound is maintained in close proximity to biological fluids containing the analyte, and/or form a biologically compatible structure that fixes the luminescent sensing compound in the subject's body (e.g., subcutaneously).

Formulating various dye-polymer compositions produces unpredictable results. Similarly stated, certain combinations of polymer and luminescent sensing compound produce synergistic results that are not apparent from an a priori examination of the individual components. For example, the luminescent output and/or lifetime of certain luminescent sensing compounds can vary significantly when formulated with different polymers. As used herein, a lifetime of a luminescent sensing compound is the time required for an intensity of the luminescent compound to decay by a factor of 1/e (approximately 36.8%) from a peak intensity.

In addition, different dye-polymer formulations can cause a temporal component of the luminescent sensing compound's characteristic emissions to be altered. By carefully selecting polymer-dye combinations the emission duration of a luminescent sensing compound can be "tuned" to be more easily detected by an instrument (or "reader") configured to detect the luminescent sensing compound. Altering the emission duration of luminescent sensing compounds through appropriate formulation can further improve the ability to deconvolute signals associated with multiple analyte sensing luminescent sensing compounds.

Some embodiments described herein relate to a sensor that includes a first polymer-luminescent sensing compound configured to produce a first luminescent signal in the presence of a first analyte and a second polymer-luminescent sensing compound configured to produce a second luminescent signal in the presence of a second analyte. The second luminescent signal can have a luminescent lifetime that is at least 1.1 times greater than a luminescent lifetime of the first luminescent signal. Such temporal differences in signal can be used to deconvolute the first luminescent signal from the second luminescent signal even when, for example, the first luminescent signal and the second luminescent signal have the same or a similar emission spectrum.

Some embodiments described herein relate to a sensor that includes a first polymer-luminescent sensing compound configured to produce a first luminescent signal in the presence of a first analyte and a second polymer-luminescent sensing compound configured to produce a second luminescent signal in the presence of a second analyte. The second polymer-luminescent sensing compound can include a luminescent sensing compound and a polymer that is configured to alter a characteristic of the luminescent sensing compound such that the second luminescent signal is distinguishable from the first luminescent signal. The polymer can alter the lifetime and/or the intensity of the luminescent sensing compound, for example, to provide temporally different luminescent characteristics and/or to cause the first luminescent signal and the second luminescent signals to have more similar intensities, which may prevent one luminescent signal from "washing out" the other.

Some embodiments described herein relate to a method that can include illuminating a sensor having a first polymer-luminescent sensing compound and a second polymer luminescent sensing compound with an excitation light. In response to illuminating the sensor, a luminescent signal including a component from the first polymer-luminescent sensing compound and a component from the second polymer luminescent sensing compound can be received. The component from the first polymer-luminescent sensing compound and the component from the second polymer luminescent sensing compound can be deconvolved based on the first polymer-luminescent sensing compound having a luminescent lifetime that is greater than a luminescent lifetime of the second polymer-luminescent sensing compound. A concentration of the first analyte can be determined based on the component of the emission spectrum associated with first polymer-luminescent sensing compound, and a concentration of the second analyte can be determined based on the component of the emission spectrum associated with second polymer-luminescent sensing compound.

Some embodiments herein relate to a sensor that includes a single luminescent compound configured to emit a luminescent signal that can be correlated to multiple analytes. In some such embodiments, a first portion of the sensor configured to sense a first analyte can include a dye-polymer formulation having a long lifetime and a second portion of the sensor configured to sense a second analyte can include a dye-polymer formulation having a short lifetime. Thus, luminescent signals emitted from the first portion of the sensor and the second portion of the sensor can have different temporal signatures which can be deconvoluted by a reader. As used herein, terms such as "long lifetime" and "short lifetime" generally refer to a relative difference between dye-polymer formulations and do not necessarily imply information about an absolute lifetime of a dye-polymer formulation. In some instances, it may be desirable for a long lifetime dye-polymer formulation to have a lifetime that is 110%, 125%, 150%, 160% or greater than a lifetime of a short lifetime-dye polymer. Similarly stated, in embodiments in which a long-lifetime dye-polymer formulation has a lifetime that is at least 110%, 125%, 150%, 160% or greater than a lifetime of a short lifetime dye-polymer formulation, a luminescent signal from the long lifetime dye can be readily deconvoluted from a luminescent signal from the short lifetime dye based on differences in their respective temporal signatures.

The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Sensors that have the Ability to Detect More than One Analyte

Some embodiments described herein relate to sensors that have the ability to detect more than one analyte. Such sensors can include a polymer scaffold made up of one or more polymers and one or more luminescent sensing compounds (e.g., dyes) paired with a synergistic polymer or polymers. The sensors can contain multiple luminescent sensing compounds each formulated differently with one or more polymers.

In an embodiment, the polymer of the scaffold may be the same as the polymer of the first luminescent sensing compound. Similarly stated, the scaffold may be a polymerized luminescent sensing compound. In an embodiment, the polymer of the scaffold may be the different from the polymer of the first luminescent sensing compound. In an embodiment, the polymer of the scaffold may be the same as the polymer of the second luminescent sensing compound. In an embodiment, the polymer of the scaffold may be the different from the polymer of the second luminescent sensing compound. The one or more luminescent sensing compounds may be chemically (e.g., covalently or non-covalently) bound to polymers of the polymer. In an embodiment, the one or more luminescent sensing compounds may be physically bound to or embedded in the polymer. In some embodiments different portions of the polymer scaffold may include different dye-polymer formulations.

Polymer Scaffold

In an embodiment, the polymer scaffold may include 2-hydroxyethyl methacrylate (HEMA), poly (hydroxyethyl methacrylate) (pHEMA), polyacrylamide, N-vinylpyrrolidone, N,N-Dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof.

In an embodiment, the polymer scaffold may be formed by polymerization from a polymer pre-polymer solution. In an aspect, the polymer pre-polymer solution may include monomers and crosslinkers. In an aspect, the polymer pre-polymer solution may also include comonomers. In an aspect, the pre-polymer solution may also include a polymer dispersed in the solution.

Non-limiting examples of monomers and comonomers include 2-fluoroethly methacrylate; 3-chloro-2-hydroxypropylmethacrylate; acryloyloxyethyltrimethyl ammonium; dimethacrylamide; 2-hydroxyethylmethacrylate; 2,2,3,4,4,4-hexafluorobutyl methacrylate; 1,1,1,3,3,3-hexafluoroisopropyl acrylate; 1H,1H-heptafluoro-n-butyl methacrylate; methyl methacrylate; 2-methacryloyloxyethyl phosphorylcholine; O-nitrobenzyl methacrylate; pentafluorobenzyl methacrylate; 1H,1H-perfluorooctyl methacrylate; [2-(methacryloyloxy)ethyl]dimethyl-(3-3sulfopropyl)ammonium; 3-sulfopropyl methacrylate; 2,2,2-trifluoroethyl methacrylate; 2,2,3,3-tetrafluoropropyl methacrylate; acrylamide; butylmethacrylamide; butylmethacrylate; carboxyethyl acrylate; hexyl methacrylate; hydroxypropyl methacrylate; n-hexylacrylate; [2-(methacryloyloxy)ethyl] trimethylammonium; lauryl methacrylate; benzyl methacrylate; 2-(tert-butylamino) ethyl methacrylate; 2-(methacryloxy)ethyl phosphate; 2-aminoethyl methacrylate; 2-bromoethyl methacrylate; trichloroethyl methacrylate; polyethylene glycol (PEG); napthylvinylpyridine (NVP); and methacrylic acid (MAA); tetraethylene glycol dimethacrylate; poly(ethylene glycol) (n) diacrylate (of varying molecular weights); ethoxylated trimethylolpropane triacrylate; and bisacrylamide Non-limiting examples of crosslinkers include bisacrylamide; bisphenol A glycerolate diacrylate; tricycle decanedimethanol diacrylate; di(trimethylolpropane) tetra-acrylate; ethylene glycol dimethacrylate; ethylene bisacrylamide; 1,6-hexanediol diacrylate; neopentyl glycol diacrylate; 2,2,3,3,4,4,5,5-octafluoro-1,6-hexyl dimethacrylate; pentaerythritol triacrylate; pentaerythritol tetraacrylate; poly(ethylene glycol) diacrylate; poly(ethylene glycol) diacrylamide; tetraethylene glycol dimethacrylate; trimethylolpropane tri-acrylate; and diurethane dimethacrylate.

In one example, a polymer matrix comprising a compound with a fluorocarbon benzyl ring with the following structure can be used to increase the lifetime of a porphyrin dye to about 410 μs compared to about 260 μs for a 2-hydroxyethyl methacrylate (HEMA).

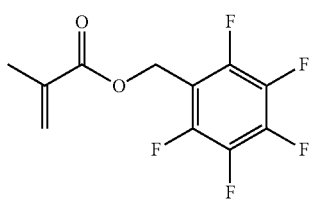 [SMILES: C=C(C)C(=O)OCc1c(F)c(F)c(F)c(F)c1F]

In another example, a polymer matrix comprising a compound with a chlorine group with the following structure can be used to increase the lifetime of a porphyrin dye to about 310 μs compared to about 260 μs for a 2-hydroxyethyl methacrylate (HEMA).

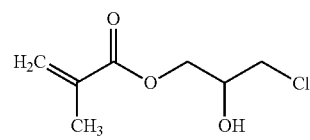

In an embodiment, the intiator may be selected from one or more compounds including irgacure Series (UV), Azobisisobutyronitrile (AIBN) (thermal), Ammonium Persulfate (APS) (thermal), and mixtures thereof.

In an embodiment, the polymer scaffold may have pore sizes of 0.1 μm-200 μm. In an aspect, the polymer scaffold may have pore sizes of 5 μm-150 μm. In an aspect, the polymer scaffold may have pore sizes of 10 μm-100 μm.

Luminescent Sensing Compounds

Luminescent sensing compounds can include luminescent dyes, luminescent sensing molecules, proteins (e.g., chemically bound to a reporter dye), quantum dots, and/or any other moiety suitable to produce a signal in response to the presence of an analyte. Such a signal can correspond to a quantity and/or concentration of analyte. In some embodiments, the luminescent dye can operable to emit a luminescent signal in response to a secondary analyte, the quantity and/or concentration of which can be influenced by a reaction with an analyte of interest. For example, an oxygen-sensitive luminescent compound can chemically bound to or physically associated with an oxidase configured to react with the analyte of interest (e.g., glucose oxidase, lactate oxidase, etc.). In such an embodiment, the oxygen-sensitive luminescent compound can emit a luminescent signal that can be correlated to the analyte of interest (e.g., glucose, lactose, etc.). U.S. Pat. No. 9,375,494, entitled "Oxygen sensors," issued on Jun. 28, 2016 and U.S. patent application Ser. No. 15/855,555, entitled "Near-IR Glucose Sensors," filed Dec. 27, 2017, the entire disclosure of each of which is incorporated herein by reference, describes some suitable luminescent sensing compounds.

As discussed above, luminescent sensing compounds can be chemically (e.g., covalently or non-covalently) bound to and/or physically bound or embedded in a polymer and/or polymer scaffold. In some embodiments different luminescent sensing compounds can be chemically and/or physically bound to different polymers that make up a one-piece polymer scaffold.

Luminescent sensing compounds can also include a polymer and/or be polymerized. Similarly stated, a polymer scaffold can include or be made up of one or more polymerized luminescent sensing compounds. In other embodiments, polymer making up a polymer scaffold of the sensor can be a different polymer composition from the polymer of or containing the luminescent sensing compound.

As discussed in further detail herein, the intensity and/or lifetime of a luminescent sensing compound can be altered based on a composition of a polymer matrix. In some embodiments, by altering the polymer matrix with short-lifetime-based luminescent sensing compounds (e.g., luminescent sensing compounds having a lifetime in the range of 0 to about 10 ns) (e.g., glucose-sensitive boronic acid dyes, pH-sensitive dyes, ion-sensitive dyes) the lifetime or intensity of these short-lifetime dyes may be shifted.

Some embodiments described herein relate to a 2-plex multi-analyte sensor that includes, a single $O_2$-sensitive luminescent dye formulated with two different polymers, such that the sensor includes a first sensor portion and a second sensor portion. In one example, the 2-plex multi-analyte sensor is a glucose and $O_2$ sensor. For example, the $O_2$-sensitive luminescent dye in the first sensor portion is operable to sense oxygen directly. The second sensor portion includes the $O_2$-sensitive luminescent dye and a second sensing moiety, glucose oxidase, for detection of glucose. The reaction of glucose via enzymatic interaction with glucose oxidase causes $O_2$ to be proportionally consumed and converted to $H_2O_2$. The reduction of $O_2$ in the vicinity of the enzyme is measured by the second sensor portion. Each dye-polymer formulation can have a different lifetime, such that signals from the different dye-polymer formulations can be distinguished.

In another embodiment, a 4-plex sensor can be used to measure four analytes. Such a sensor can include, for example, two different analyte sensitive luminescent dyes with non-overlapping excitation/emission spectrums. Each of the analyte sensitive luminescent dyes can be formulated with two polymers and another sensing moiety or catalyst configured to cause the analytes of interest to react, causing a change in the analyte to which the luminescent dyes are sensitive (e.g., oxidases for $O_2$ sensitive dyes). Such a sensor can be operable to emit two signals distinguishable by their emission spectrums and two signals distinguishable by their temporal signatures. In one example, the multi-analyte sensor is configured for sensing $O_2$, glucose (using glucose oxidase), lactate (using lactate oxidase), and pyruvate (using pyruvate oxidase).

Any other combination of luminescent sensing compounds and polymers is possible. For example, a 9-plex sensor can be constructed using three different $O_2$-sensitive luminescent dyes with non-overlapping excitation/emission spectrums and three different polymers, such that the sensor can emit three sets of three signals distinguishable by emission spectrum, where each signal from a set of signals having the same emission spectrum is distinguishable by temporal signature.

FIG. 1 is a chart illustrating a luminescent glucose sensitive compound having variable luminescent intensity depending on polymer matrix, according to an embodiment. FIG. 1 shows spectra of two 10 mM glucose sensors, utilizing the same glucose sensitive dye in two different polymer matrices. The excitation wavelength was 630 nm. The following monomers are used in one or more dye-polymer formulations depicted in FIG. 1, and elsewhere in the application.

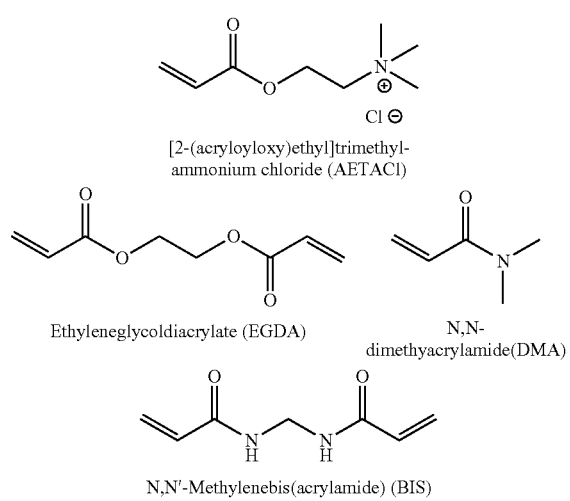

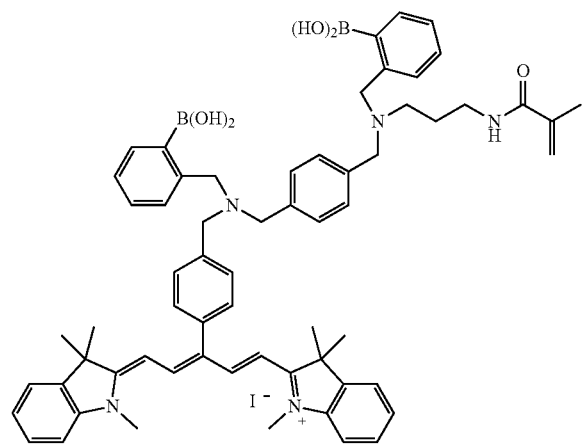 [SMILES: C=C(C)C(=O)NCCCN(Cc1ccc(CN(Cc2ccc(C(=C\C=C3/N(C)c4ccccc4C3(C)C)/C=C/C3=[N+](C)c4ccccc4C3(C)C)cc2)Cc2ccccc2B(O)O)cc1)Cc1ccccc1B(O)O ; [I-]]

The glucose-sensitive dye used in the sensors of FIG. 1 is as follows:

As shown in FIG. 1, the polymer formulation significantly alters the intensity of the luminescent sensing compound. In particular, a 90/10 formulation of DMA/PEGDAAm causes the luminescent sensing compound to phosphoresce with surprising intensity—intensity that is approximately twice as a 60/40 HEMA/DMA polymer-luminescent sensing compound formulation.

Example 1—Effect of Different Polymer Matrices on the Signal and Response of a Particular Analyte-Sensitive Luminescent Sensing Compound to an Analyte Table 1, shown below, illustrates that a dye's sensitivity changes when formulated with different polymers. The above glucose-sensitive dye was formulated with polymers and then subjected to various concentrations of glucose over time. The sensitivity is shown in Table 1 as the "Modulation (1200/150)" which represents the intensity of the sensor at 200 mg/dL divided by the intensity of the sensor at 50 mg/dL glucose. The sensor including HEMA has low response to glucose but when the dye was formulated with AAm/Acryl-PEG/BIS, the dye had a greater than 90% increase in fluorescence intensity over the range of glucose tested.

TABLE 1

| Formulation | Dye | Modulation (I200/50) |
|---|---|---|
| HEMA/DMA (60/40), EGDA 2%, Dye 10 mM, 50% | Glucose sensitive dye | 9% |
| AAm/Acryl-PEG (60/40), BIS (0.3%), Dye 10 mM, 25% | Glucose sensitive dye | 93% |

In some instances, a dye sensitive to one analyte may typically have a significantly lower intensity than a dye sensitive to another analyte. A multi-analyte sensor incorporating such dyes may result in the more intense dye washing out the less intense dye, which may present challenges to deconvoluting signals associated with the different dyes. In some embodiments, therefore, dye-polymer formulations can be selected to increase the intensity of the lower-intensity dye and/or decrease the intensity of the higher-intensity dye. Such a sensor, when exposed to analytes, may produce luminescent signals that are within 5%, 10%, 25%, 50%, or within any other suitable intensity of each other. Such luminescent signals may then be more easily deconvoluted, for example, based on having different emission spectra and/or lifetimes.

Figure 2:
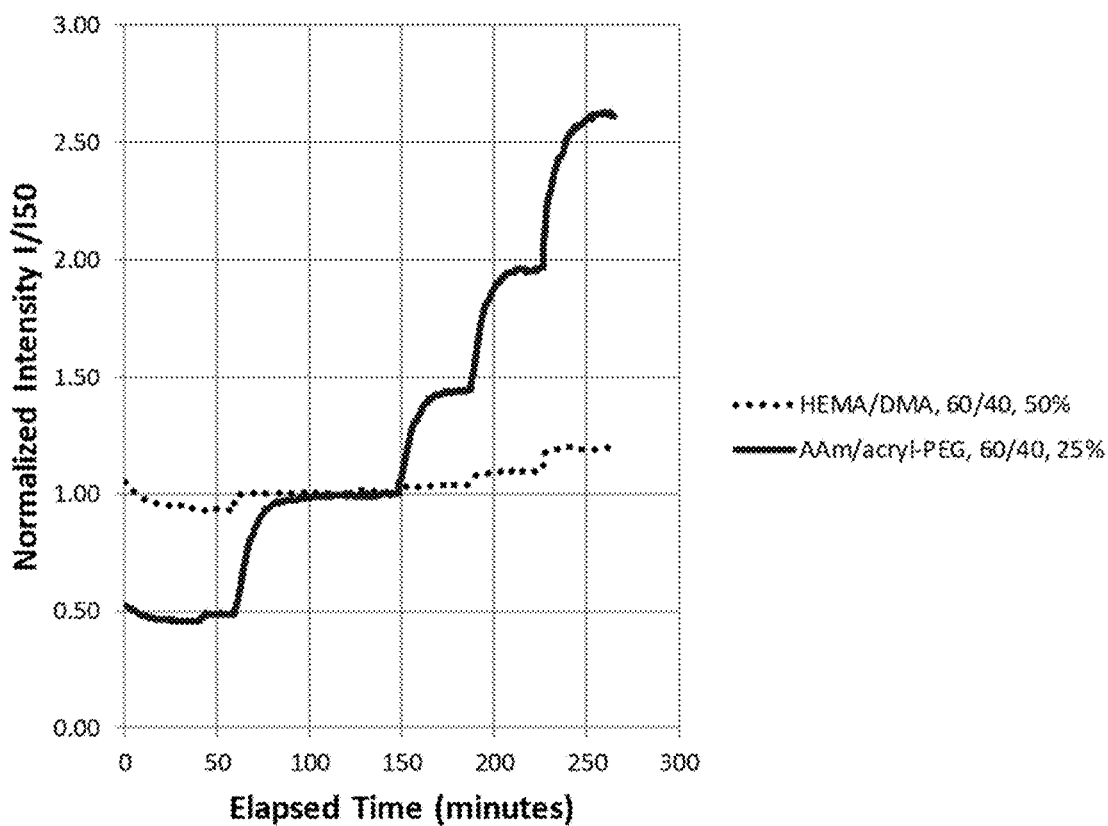
FIG. 2, a chart illustrating an example of the choice of polymer's effect the modulation of a luminescent sensing compound.

FIG. 2, a chart showing the response of the formulations detailed below in Table 1 to changes in glucose concentration, illustrates that the choice of polymer can dramatically alter the modulation of a luminescent sensing compound. The blue trace changes intensity when exposed to concentrations between 0 and 400 mg/dL. Accordingly, individually selecting dye-polymer formulations for luminescent sensing compounds can significantly improve and/or alter the performance of a luminescent sensing compound.

FIG. 2 compares the performance of one glucose sensitive dye in two different polymer matrices, illustrating that the polymer can improve the sensitivity of the dye, which facilitates data analysis. 50 mg/dL glucose was introduced at minute 59; 100 mg/dL glucose was introduced at minute 148; 200 mg/dL glucose was introduced at minute 187; and 400 mg/dL glucose was introduced at minute 226. The data has been normalized so that at 50 mg/dL glucose the intensity value has a numerical value of one. The y-axis is the intensity normalized to 50 mg/dL glucose. Normalizing allows for us to compare two different sensors which have different fluorescence intensity values.

Figure 3:
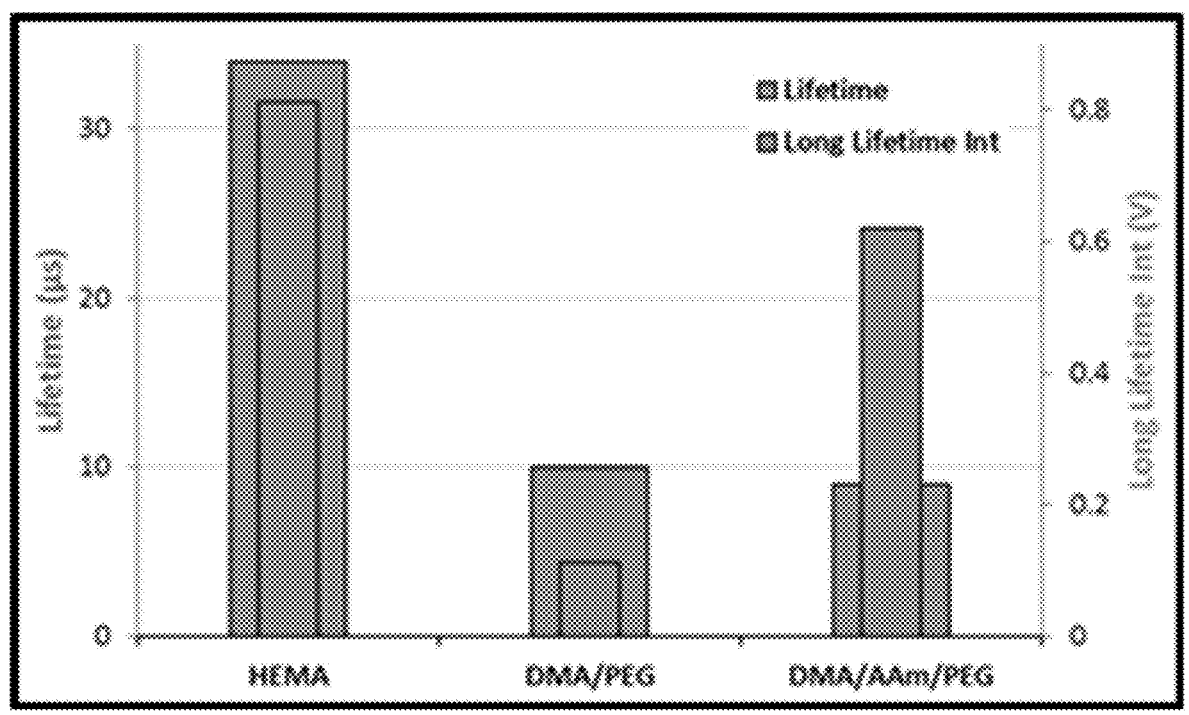
FIG. 3 illustrates an example of the choice of polymer's effect on intensity and lifetime of a luminescent sensing compound.

FIG. 3 illustrates that luminescent intensity and luminescent lifetime can be dramatically altered based on the choice of polymer.

Figure 4:
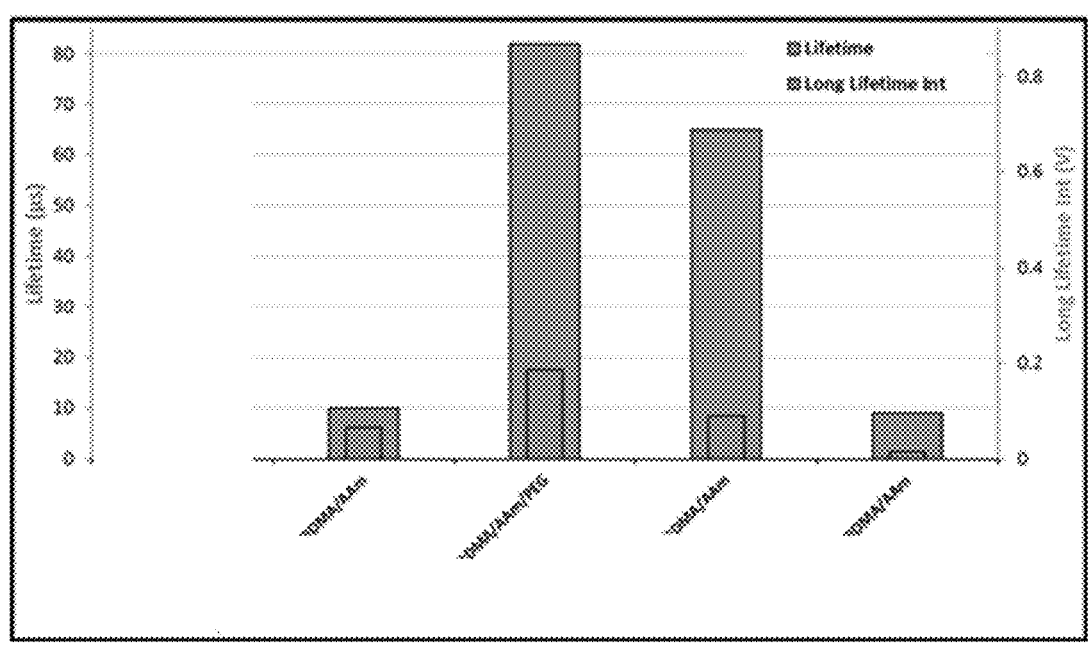
FIG. 4 illustrates a multi analyte system, including an oxygen sensitive luminescent compound and a glucose sensitive luminescent compound.

FIG. 4 illustrates a multi analyte system, including an oxygen sensitive luminescent compound and a glucose sensitive luminescent compound. The performance of an oxygen sensor was assessed in the presence of different polymers. The performance of a glucose sensor was also assessed in the presence of different polymers. The particular polymer/sensor combination greatly affected the performance.

Figure 5:
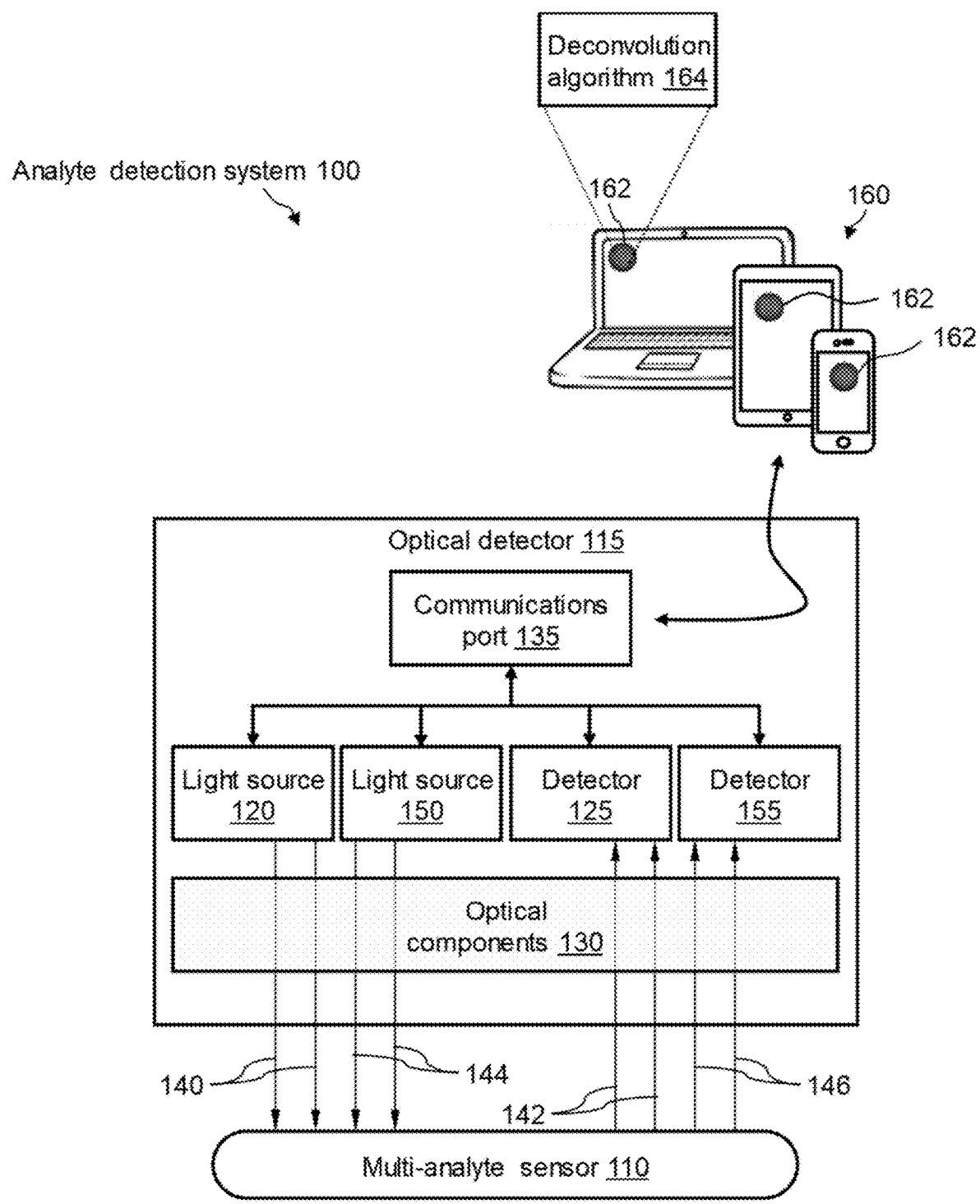
FIG. 5 is a block diagram of a system operable to detect analyte-dependent signals from a sensor, according to an embodiment.

FIG. 5 is a block diagram of a system 100 operable to detect analyte-dependent signals from a sensor 110. In some embodiments, the sensor 110 is a multi-analyte sensor operable to emit temporally distinguishable signals. For example, the sensor 110 can be operable to emit two signals having the same or similar emission spectra, but different lifetimes.

Sensor 110 can, for example, be implanted a few millimeters (e.g., 1-10 mm) under the skin of a subject (not shown). Sensor 110 can include a first sensor portion and a second sensor portion that are composed of different polymers but contain the same $O_2$-sensitive luminescent sensing compound (or other suitable analyte-sensing compound). In one example, the $O_2$-sensitive luminescent dye is Pd-BP-AEME-4. Pd-BP-AEME-4 has the following structure:

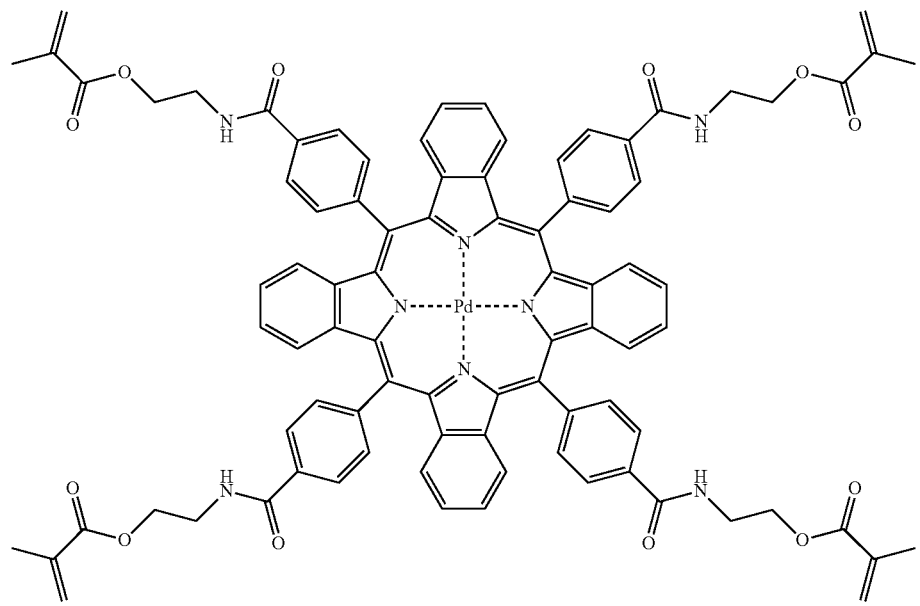

The first sensor portion and the second sensor portion of sensor 110 can be formulated with different polymers such that signals emitted from the first sensor portion and the second sensor portion have different luminescent lifetimes. Similarly stated, the first sensor portion can be configured to emit a long-lifetime signal, while the second sensor portion can be configured to emit a short-lifetime signal. Accordingly, multi-analyte sensor 110 is capable of emitting, in response to a single excitation light, two analyte-dependent optical signals with the same emission wavelength, wherein the two analyte-dependent optical signals may be distinguished by their different lifetime decay curves, as illustrated, for example, in FIG. 6.

In one example, sensor 110 is a glucose and $O_2$ sensor. For example, the $O_2$-sensitive luminescent dye in the first sensor portion acts as a first sensing moiety operable to directly measure $O_2$. The second sensor portion includes the $O_2$-sensitive luminescent dye and a second sensing moiety, glucose oxidase, for detection of glucose. The reaction of glucose via enzymatic interaction with glucose oxidase causes $O_2$ to be proportionally consumed and converted to $H_2O_2$. The reduction of $O_2$ in the vicinity of the enzyme is measured by the $O_2$-sensitive luminescent dye in a second sensor portion. Each dye-polymer formulation can have a different lifetime, such that signals from the different dye-polymer formulations can be distinguished.

The analyte detection system 100 also includes an optical detector 115. The optical detector 115 can be a patch that can be placed on the surface of the user's skin above or in close proximity to the multi-analyte sensor 110. The optical detector 115 includes a light source 120 operable to illuminate luminescent sensing compounds in the sensor 110, a detector 125 for collecting the emission light from luminescent sensing compounds in the sensor 110, and suitable optical components 130 (e.g., lenses, optical filters, etc.), and a communications port 135.

The light source 120 is operable to transmit an excitation light 140 to sensor 110. The light source 120 can be configured to generate light that is within the excitation wavelength range one or more luminescent sensing compounds of the sensor 110, such as an $O_2$-sensitive luminescent dye. In embodiments in which the sensor 110 includes multiple luminescent sensing compounds and/or multiple dye-polymer sensing portions, the light source 120 can be configured to simultaneously excite multiple or all luminescent sensing compounds/dye-polymer sensing portions. In one example, light source 120 emits excitation light 140 in the wavelength range of about 600 to about 650 nm. Suitable light sources may include, but are not limited to, lasers, semi-conductor lasers, light-emitting diodes (LEDs), and organic LEDs.

Detector 125 is operable to detect emission light 142 from sensor 110. In particular, detector 125 is operable to detect light that is within the emission wavelength range of one or more luminescent sensing compounds of the sensor 110, such as an $O_2$-sensitive luminescent dye. As discussed in further detail herein, the detector 125 can be operable to detect optical signals emitted from includes multiple luminescent sensing compounds and/or multiple dye-polymer sensing portions, including optical signals having different temporal and/or emission spectrum characteristics (e.g., a long-lifetime signal and a short-lifetime signal). In one example, detector 125 may detect emission light 142 in the wavelength range of from about 750 to about 850 nm. Suitable detectors may include, but are not limited to, photodiodes, complementary metal-oxide-semiconductor (CMOS) detectors, and charge-coupled device (CCD) detectors.

Detector 125 can be filtered (e.g., with dichroic filters or other suitable filters) to measure the optical signals emitted within the wavelength ranges. Optical filters are one example of optical components 130. However, optical components 130 may include any other types of components needed in optical detector 115.

Data received by the detector 125 can be transmitted to a computing device 160 that is operable to process such information. Computing device 160 can include a processor and a memory and may be any type of computing device, such as a desktop computer, a laptop computer, a tablet device, a mobile phone, a smartphone, and the like. A desktop application 162 or mobile app 162 resides on computing device 160 for processing any information from optical detector 115. As shown in FIG. 5, the processing capability of analyte detection system 100 is external to optical detector 115 that is operable to be disposed on the surface of the skin. It should be understood, however, that in other embodiments, the detector 115 can include additional processing capability (e.g., processors and/or memory) such that the detector 115 itself may be operable to process and/or analyze signals received from the sensor 110. Furthermore, in other embodiments, data received by the detector 115 can be processed via a remote server, on "the cloud," and/or any other suitable computing environment.

Communications port 135 facilitates a communications link to light source 120 and detector 125. For example, communications port 135 can be a wired communications port, such as a USB or HDMI port, or a wireless communications port, such as blue-tooth or Wi-Fi. Using communications port 135, the separate computing device 160 may be communicatively connected to light source 120 and detector 125 of optical detector 115. Namely, computing device 160 may be used to activate light source 120 and to collect information from detector 125, wherein detector 125 converts optical signals received from analyte sensor 110 to an electrical and/or wireless signal output.

Computing device 160 may use desktop application 162 or mobile app 162 to process any information from multi-analyte sensor 110. Namely, desktop application 162 or mobile app 162 may include any software and/or hardware components for processing any information from multi-analyte sensor 110. In one example, desktop application 162 or mobile app 162 includes a deconvolution algorithm 164 suitable to deconvolute emission signals having different lifetimes and/or emission spectra from sensor 110. The luminescent lifetime is a measure of the time a luminescent material spends in the excited state before returning to the ground state by emitting a photon. A lifetime measurement is derived from the decay in the luminescent signal overtime. The lifetimes of luminophores can range from a few picoseconds to milliseconds. The deconvolution algorithm 164, therefore can be operable to determine a quantity and/or concentration of multiple analytes (e.g., oxygen, glucose, lactate, or pyruvate) by separating out signals having different decay rates (e.g., through frequency domain processing and analysis).

Figure 6:
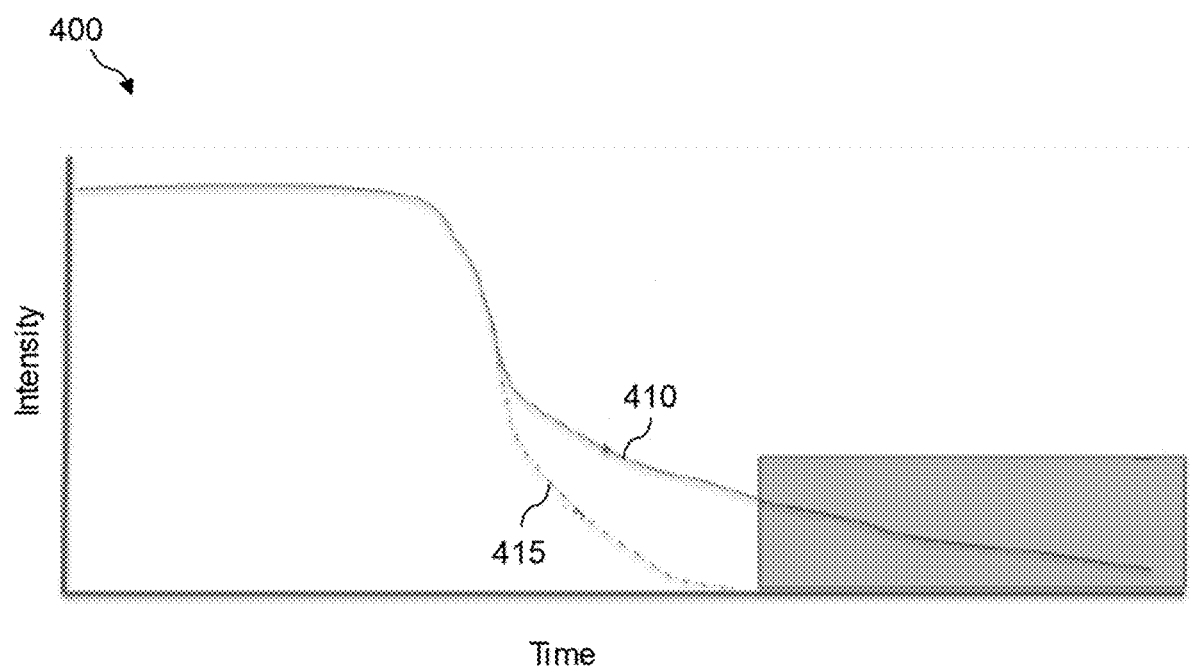
FIG. 6 is a plot of an example of the emission intensity of a multi-analyte sensor.

FIG. 6 is a plot 400 of an example of the luminescent lifetime decay curve of a multi-analyte sensor. Plot 400 indicates the combined short-lifetime and the long-lifetime components of the optical signal emitted by the multi-analyte sensor 110, and the deconvoluted short-lifetime component. Namely, a curve 410 indicates the emission intensity of the multi-analyte sensor, wherein the optical signal includes emission from the long-lifetime component (e.g., $O_2$ sensing component) and a short-lifetime component (e.g., glucose sensing component) of the sensor. A curve 415 indicates the emission intensity of the short-lifetime component deconvoluted from the combined optical signal (i.e., curve 410) returned from multi-analyte sensor 110. The area of curve 410 highlighted in gray represents the long-lifetime component of the sensor.

Table 2 below includes a list of sensor component formulations. Each formulation includes Pd-BP-AEME-4 as a luminescent sensing compound (or "dye"). As shown in the column labeled tau0, the lifetime of the dye in a zero-oxygen environment in microseconds, the lifetime of the luminescent sensing compound varies dramatically and unexpectedly depending on the polymers chemically and/or physically bound to the luminescent sensing compound. Because luminescent signals having different lifetimes can be deconvoluted as discussed in further detail herein, a sensor containing multiple Pd-BP-AEME-4-polymer portions can be used to detect multiple analytes. In some embodiments, it can be desirable to select dye-polymer formulations whose luminescent lifetimes vary by at least 10%, by at least 25%, by at least 60%, or by at least 100% when formulating a multi-analyte sensor.

Table 2 further shows that the tau0 could be changed by changing the components as well as the ratio of those components. For example, in formulations with Component 1=hydroxyethyl methacrylate and Component 2=ethylene glycol dimethacrylate, the wt % of ethylene glycol directly impacted the tau0 of the formulation. An increase in ethylene glycol dimethacrylate changed the tau0 from 268 µs to 279 µs. With the same formulations, by keeping the wt % of ethylene glycol constant at approximately 9.8, adding a Component 2=hydroxypropyl methacrylate and Component 3=ethylene glycol methacrylate increased the tau0 from 279 µs to 297 µs. These examples offer some direct comparisons of the ability to change components and ratios of the components to change the behavior of the polymer. Overall, changing components and ratios of the polymer while utilizing the same dye resulted in tau0 measurements from 101 µs to 411.6 µs.

TABLE 2

| Component 1 | Component 2 | Component 3 | wt % cmpt 1 | wt % cmpt 2 | wt % cmpt 3 | Tau0 (µs) |
|---|---|---|---|---|---|---|
| 2-hydroxyethyl methacrylate | 2,2,3,3,4,4,5,5-octafluoro-1,6-hexyldimethacrylate | | 95.23 | 4.77 | | 101.5 |
| 2,2,3,3,4,4,4-heptafluorobutyl methacrylate | 2-hydroxyethyl methacrylate | ethylene glycol dimethacrylate | 53.69 | 41.98 | 4.33 | 115.6 |
| 2-carboxyethyl acrylate | [2-(acryloyloxy)ethyl]trimethylammonium chloride | tetraethylene glycol dimethacrylate | 59.00 | 38.88 | 2.12 | 160.6 |
| 2-carboxyethyl acrylate | [2-(acryloyloxy)ethyl]trimethylammonium chloride | tetraethylene glycol dimethacrylate | 57.08 | 37.62 | 5.30 | 184.0 |
| o-nitrobenzyl methacrylate | tetraethylene glycol dimethacrylate | | 90.98 | 9.02 | | 185.4 |
| [2-(methacryloyloxy)ethyl]dimethyl-(3-sulfopropyl)ammonium hydroxide | Polyurethane D640 (10%) | N,N'-methylenebis(acrylamide) | 83.64 | 16.24 | 0.12 | 186.6 |
| poly(ethylene glycol) diacrylate (Mn = 700) | Polyurethane D640 (5%) | | 78.89 | 21.11 | | 192.3 |
| 2-carboxyethyl acrylate | [2-(acryloyloxy)ethyl]trimethylammonium chloride | tetraethylene glycol dimethacrylate | 43.14 | 41.08 | 15.78 | 197.2 |
| 2-carboxyethyl acrylate | [2-(acryloyloxy)ethyl]trimethylammonium chloride | tetraethylene glycol dimethacrylate | 53.91 | 35.52 | 10.57 | 197.8 |
| poly(ethylene glycol) diacrylate (Mn = 700) | Polyurethane D640 (5%) | | 91.79 | 8.21 | | 201.8 |
| acrylamide | Polyurethane D640 (5%) | N,N'-methylenebis(acrylamide) | 77.84 | 22.06 | 0.10 | 204.1 |
| poly(ethylene glycol) diacrylamide (Mn = 3700) | Polyurethane D640 (5%) | | 81.65 | 18.35 | | 206.4 |
| [2-(methacryloyloxy)ethyl]dimethyl-(3-sulfopropyl)ammonium hydroxide | Polyurethane D640 (10%) | N,N'-methylenebis(acrylamide) | 80.15 | 19.62 | 0.22 | 210.2 |
| poly(ethylene glycol) diacrylate (Mn = 700) | Polyurethane D640 (5%) | | 73.66 | 26.34 | | 213.4 |
| o-nitrobenzyl methacrylate | ethylene glycol dimethacrylate | | 91.29 | 8.71 | | 215.2 |
| poly(ethylene glycol) diacrylate (Mn = 700) | Polyurethane D640 (5%) | | 78.87 | 21.13 | | 217.6 |
| poly(ethylene glycol) diacrylate (Mn = 700) | Polyurethane D640 (5%) | | 83.29 | 16.71 | | 221.7 |
| 2-hydroxyethyl methacrylate | tetraethylene glycol dimethacrylate | | 89.83 | 10.17 | | 223.6 |
| [2-(methacryloyloxy)ethyl]dimethyl-(3-sulfopropyl)ammonium hydroxide/acrylamide (1:1) | Polyurethane D640 (5%) | N,N'-methylenebis(acrylamide) | 77.84 | 22.06 | 0.10 | 225.0 |
| poly(ethylene glycol) diacrylate (Mn = 700) | Polyurethane D640 (10%) | | 71.36 | 28.64 | | 233.5 |
| 2-carboxyethyl acrylate | [2-(acryloyloxy)ethyl]trimethylammonium chloride | tetraethylene glycol dimethacrylate | 47.62 | 31.38 | 21.01 | 235.8 |
| 2-hydroxyethyl methacrylate | tetraethylene glycol dimethacrylate | 2-methacryloyloxyethyl phosphorylcholine | 80.15 | 18.14 | 1.71 | 242.6 |

TABLE 2-continued

| Component 1 | Component 2 | Component 3 | wt % cmpt 1 | wt % cmpt 2 | wt % cmpt 3 | Tau0 (μs) |
|---|---|---|---|---|---|---|
| 2-hydroxyethyl methacrylate | tetraethylene glycol dimethacrylate | | 95.15 | 4.85 | | 250.3 |
| 2-hydroxyethyl methacrylate | tetraethylene glycol dimethacrylate | | 69.61 | 30.39 | | 251.7 |
| 2-hydroxyethyl methacrylate | tetraethylene glycol dimethacrylate | | 94.91 | 5.09 | | 252.9 |
| 2-hydroxyethyl methacrylate | tetraethylene glycol dimethacrylate | | 97.96 | 2.04 | | 253.1 |
| 2-hydroxyethyl methacrylate | tetraethylene glycol dimethacrylate | 2-methacryloyloxyethyl phosphorylcholine | 96.63 | 2.68 | 0.69 | 254.7 |
| 2,2,3,3,4,4,4-heptafluorobutyl methacrylate | ethylene glycol dimethacrylate | | 96.31 | 3.69 | | 255.5 |
| 2-hydroxyethyl methacrylate | tetraethylene glycol dimethacrylate | | 98.00 | 2.00 | | 256.7 |
| lauryl methacrylate | tetraethylene glycol dimethacrylate | 2-methacryloyloxyethyl phosphorylcholine | 55.90 | 38.32 | 5.78 | 262.2 |
| 2-(tert-butylamino)ethyl methacrylate | ethylene glycol dimethacrylate | | 94.40 | 5.60 | | 263.8 |
| lauryl methacrylate | tetraethylene glycol dimethacrylate | 2-methacryloyloxyethyl phosphorylcholine | 86.52 | 11.24 | 2.24 | 265.6 |
| 2-hydroxyethyl methacrylate | ethylene glycol dimethacrylate | | 95.10 | 4.90 | | 267.9 |
| 2,2,3,3,4,4,4-heptafluorobutyl methacrylate | ethylene glycol dimethacrylate | | 83.93 | 16.07 | | 268.3 |
| 2-hydroxyethyl methacrylate | ethylene glycol dimethacrylate | n-hexyl acrylate | 77.88 | 14.96 | 7.16 | 272.6 |
| 2,2,3,4,4,4-hexafluorobutyl methacrylate | ethylene glycol dimethacrylate | | 96.13 | 3.87 | | 273.0 |
| acrylamide | N,N'-methylenebis(acrylamide) | | 99.86 | 0.14 | | 275.0 |
| 2,2,3,3,4,4,4-heptafluorobutyl methacrylate | poly(ethylene glycol) diacrylate (Mn = 700) | | 82.77 | 17.23 | | 277.5 |
| 2-hydroxyethyl methacrylate | ethylene glycol dimethacrylate | | 90.18 | 9.82 | | 279.3 |
| 2-hydroxyethyl methacrylate | 2-fluoroethyl methacrylate | poly(ethylene glycol) diacrylate (Mn = 700) | 75.23 | 19.50 | 5.27 | 279.4 |
| 2-hydroxyethyl methacrylate | N,N-dimethylacrylamide | ethylene glycol dimethacrylate | 73.40 | 16.62 | 9.98 | 282.1 |
| 1,1,1,3,3,3-hexafluoroisopropyl acrylate | tetraethylene glycol dimethacrylate | | 91.79 | 8.21 | | 284.5 |
| 2,2,3,3,4,4,4-heptafluorobutyl methacrylate | poly(ethylene glycol) diacrylate (Mn = 700) | | 91.53 | 8.47 | | 287.3 |
| 2,2,3,3,4,4,4-heptafluorobutyl methacrylate | ethylene glycol dimethacrylate | 2,2,2-trifluoroethyl methacrylate | 68.55 | 16.40 | 15.05 | 288.5 |
| 2-hydroxyethyl methacrylate | ethylene glycol dimethacrylate | hydroxypropyl methacrylate | 76.85 | 14.76 | 8.40 | 289.5 |
| 2-hydroxyethyl methacrylate | n-hexyl acrylate | ethylene glycol dimethacrylate | 78.47 | 12.99 | 8.54 | 289.8 |
| 2-hydroxyethyl methacrylate | ethylene glycol dimethacrylate | hydroxypropyl methacrylate | 81.29 | 9.83 | 8.88 | 291.1 |
| 2-hydroxyethyl methacrylate | n-hexyl acrylate | ethylene glycol dimethacrylate | 74.46 | 15.41 | 10.13 | 291.9 |
| 2-hydroxyethyl methacrylate | hydroxypropyl methacrylate | ethylene glycol dimethacrylate | 63.42 | 26.73 | 9.86 | 297.2 |
| 2-hydroxyethyl methacrylate | ethylene glycol dimethacrylate | 2-methacryloyloxyethyl phosphorylcholine | 80.71 | 17.57 | 1.72 | 298.7 |
| 2,2,3,3,4,4,4-heptafluorobutyl methacrylate | ethylene glycol dimethacrylate | | 96.13 | 3.87 | | 303.4 |
| 2,2,2-trifluoroethyl methacrylate | poly(ethylene glycol) diacrylate (Mn = 700) | | 98.10 | 1.90 | | 307.1 |
| 2,2,3,3,4,4,4-heptafluorobutyl methacrylate | tetraethylene glycol dimethacrylate | | 95.98 | 4.02 | | 307.2 |
| 2,2,3,3-tetrafluoropropyl methacrylate | poly(ethylene glycol) diacrylate (Mn = 700) | | 95.45 | 4.55 | | 307.3 |
| 3-chloro-2-hydroxypropyl methacrylate | tetraethylene glycol dimethacrylate | | 98.20 | 1.80 | | 307.7 |
| 2-hydroxyethyl methacrylate | 2-fluoroethyl methacrylate | poly(ethylene glycol) diacrylate (Mn = 700) | 56.03 | 38.73 | 5.23 | 308.3 |

TABLE 2-continued

| Component 1 | Component 2 | Component 3 | wt % cmpt 1 | wt % cmpt 2 | wt % cmpt 3 | Tau0 (μs) |
|---|---|---|---|---|---|---|
| 2,2,2-trifluoroethyl methacrylate | poly(ethylene glycol) diacrylate (Mn = 700) | | 95.25 | 4.75 | | 309.8 |
| 2,2,3,3,4,4,4-heptafluorobutyl methacrylate | trimethylolpropane triacrylate | | 95.87 | 4.13 | | 311.9 |
| 2,2,2-trifluoroethyl methacrylate | 2-hydroxyethyl methacrylate | ethylene glycol dimethacrylate | 78.13 | 17.39 | 4.48 | 314.7 |
| 2,2,2-trifluoroethyl methacrylate | ethylene glycol dimethacrylate | | 98.25 | 1.75 | | 318.2 |
| 2,2,3,3-tetrafluoropropyl methacrylate | ethylene glycol dimethacrylate | | 91.53 | 8.47 | | 319.4 |
| 2,2,2-trifluoroethyl methacrylate | ethylene glycol dimethacrylate | | 86.66 | 13.34 | | 319.7 |
| 2,2,2-trifluoroethyl methacrylate | tetraethylene glycol dimethacrylate | | 98.18 | 1.82 | | 320.1 |
| 2-hydroxyethyl methacrylate | methyl methacrylate | tetraethylene glycol dimethacrylate | 47.45 | 41.81 | 10.74 | 321.2 |
| 2,2,2-trifluoroethyl methacrylate | ethylene glycol dimethacrylate | | 91.17 | 8.83 | | 322.8 |
| 2-fluoroethyl methacrylate | poly(ethylene glycol) diacrylate (Mn = 700) | | 69.43 | 30.57 | | 325.4 |
| methyl methacrylate | ethylene glycol dimethacrylate | | 94.47 | 5.53 | | 325.6 |
| 2-fluoroethyl methacrylate | tetraethylene glycol dimethacrylate | | 95.08 | 4.92 | | 327.9 |
| 2,2,3,4,4,4-hexafluorobutyl methacrylate | ethylene glycol dimethacrylate | | 88.12 | 11.88 | | 329.7 |
| 2,2,3,4,4,4-hexafluorobutyl methacrylate | ethylene glycol dimethacrylate | | 92.17 | 7.83 | | 330.5 |
| 2,2,2-trifluoroethyl methacrylate | tetraethylene glycol dimethacrylate | | 95.44 | 4.56 | | 335.8 |
| 2-fluoroethyl methacrylate | 2-hydroxyethyl methacrylate | poly(ethylene glycol) diacrylate (Mn = 700) | 48.25 | 46.53 | 5.22 | 336.4 |
| 2,2,3,3,4,4,4-heptafluorobutyl methacrylate | 1,6-hexanediol diacrylate | | 96.94 | 3.06 | | 336.7 |
| methyl methacrylate | tetraethylene glycol dimethacrylate | | 94.26 | 5.74 | | 339.6 |
| methyl methacrylate | tetraethylene glycol dimethacrylate | | 88.62 | 11.38 | | 340.3 |
| 2-fluoroethyl methacrylate | tetraethylene glycol dimethacrylate | | 98.03 | 1.97 | | 341.0 |
| 2,2,3,4,4,4-hexafluorobutyl methacrylate | 2-hydroxyethyl methacrylate | ethylene glycol dimethacrylate | 80.30 | 15.66 | 4.04 | 342.0 |
| 2,2,2-trifluoroethyl methacrylate | ethylene glycol dimethacrylate | | 95.61 | 4.39 | | 342.1 |
| 2-fluoroethyl methacrylate | poly(ethylene glycol) diacrylate (Mn = 700) | | 94.87 | 5.13 | | 343.6 |
| 2,2,3,3,4,4,4-heptafluorobutyl methacrylate | poly(ethylene glycol) diacrylate (Mn = 700) | | 95.80 | 4.20 | | 344.1 |
| 2-fluoroethyl methacrylate | poly(ethylene glycol) diacrylate (Mn = 700) | | 79.57 | 20.43 | | 344.3 |
| 2,2,2-trifluoroethyl methacrylate | 1,6-hexanediol diacrylate | | 96.69 | 3.31 | | 344.9 |
| ethylene glycol dicyclopentenyl ether methacrylate | ethylene glycol dimethacrylate | | 95.15 | 4.85 | | 347.0 |
| 2,2,3,4,4,4-hexafluorobutyl methacrylate | ethylene glycol dimethacrylate | | 92.90 | 7.10 | | 348.3 |
| 2-fluoroethyl methacrylate | poly(ethylene glycol) diacrylate (Mn = 700) | | 97.95 | 2.05 | | 348.4 |
| 2-fluoroethyl methacrylate | 2-hydroxyethyl methacrylate | poly(ethylene glycol) diacrylate (Mn = 700) | 76.41 | 18.42 | 5.16 | 348.5 |
| 2-fluoroethyl methacrylate | poly(ethylene glycol) diacrylate (Mn = 700) | | 82.96 | 17.04 | | 351.0 |
| 2-fluoroethyl methacrylate | poly(ethylene glycol) diacrylate (Mn = 700) | | 89.76 | 10.24 | | 352.6 |
| 2,2,2-trifluoroethyl methacrylate | 2,2,3,3,4,4,4-heptafluorobutyl methacrylate | ethylene glycol dimethacrylate | 74.51 | 21.21 | 4.28 | 354.5 |
| 2,2,2-trifluoroethyl methacrylate | trimethylolpropane triacrylate | | 95.33 | 4.67 | | 362.1 |

TABLE 2-continued

| Component 1 | Component 2 | Component 3 | wt % cmpt 1 | wt % cmpt 2 | wt % cmpt 3 | Tau0 (μs) |
|---|---|---|---|---|---|---|
| 2,2,2-trifluoroethyl methacrylate | 1,6-hexanediol diacrylate | | 96.52 | 3.48 | | 363.1 |
| ethylene glycol dicyclopentenyl ether methacrylate | tetraethylene glycol dimethacrylate | | 94.97 | 5.03 | | 364.5 |
| benzyl methacrylate | ethylene glycol dimethacrylate | | 95.05 | 4.95 | | 366.0 |
| 2-fluoroethyl methacrylate | ethylene glycol dimethacrylate | | 95.26 | 4.74 | | 391.2 |
| pentafluorobenzyl methacrylate | ethylene glycol dimethacrylate | | 92.27 | 7.73 | | 391.4 |
| pentafluorobenzyl methacrylate | ethylene glycol dimethacrylate | | 98.48 | 1.52 | | 411.0 |
| pentafluorobenzyl methacrylate | ethylene glycol dimethacrylate | | 96.18 | 3.82 | | 411.6 |
| pentafluorobenzyl methacrylate | poly(ethylene glycol) diacrylate (Mn = 700) | | 91.65 | 8.35 | | 413.9 |

Example 4—Oxygen Sensors

Oxygen-sensitive polymers were synthesized with the dyes and wt % of the different monomers, crosslinkers, and/or polymers described in Table 2. For the composition of Component 1=2,2,2-trifluoroethyl methacrylate (95.2%), Component 2=poly(ethylene glycol) diacrylate ($M_n$=700) (4.8%), the following protocol was used. The polymer composition (62.5 μL) was mixed based on the weight percentages above. The solvent and dye mixture (62.5 μL) was prepared by adding 2,2'-Azorbis(2,4-dimethylvaleronitrile) (0.6 mg), dimethyl sulfoxide (49.4 μL), and Pd-BP-AEME-4 (10 mM in dimethylsulfoxide, 12.5 μL). The polymer composition (62.5 μL) and solvent and dye mixture (62.5 μL), were combined and put into a glass mold with a 0.75 mm wide Teflon spacer. The solution was then polymerized by heating at 60° C. for 120 minutes. The material was then removed from the mold, placed in water overnight and cut into smaller sizes for testing.

Other combinations of polymers were created using a similar method as described above. Co-solvents were chosen based on solubility and were combinations of ethanol, ethylene glycol, dimethyl sulfoxide, tetrahydrofuran, water, phosphate buffered saline, dimethylformamide, N-methyl-2-pyrrolidone. Ultra-violet initiators and heat initiators of 2,2'-Azorbis(2,4-dimethylvaleronitrile), 2,2-dimethoxy-2-phenylacetophenone, 2,2'-azobis[2-(2-imidazolin-2-yl)propane]dihydrochloride, 1-Hydroxycyclohexyl phenyl ketone, 2-Hydroxy-4'-(2-hydroxyethoxy)-2-methylpropiophenone, and azobisisobutyronitrile were used alone or in combination with another initiator depending on the component combinations and polymerization approach (UV or heat). The polymers were synthesized with between 30-90% polymer composition balanced with the solvent and dye mixture.

After polymerization, the sensors were equilibrated in phosphate buffered saline (20 mM) and tested in vitro by bubbling pure nitrogen at 37° C. until an equilibrium was reached. The phosphorescent lifetime at tau0 were measured with a custom optical reader. The tau0 is defined as the phosphorescent lifetime at 0% oxygen in solution at 37° C. The tau0 is presented in Table 2.

Table 2 shows that the tau0 could be changed by changing the components as well as the ratio of those components. For example, in formulations with Component 1=hydroxyethyl methacrylate and Component 2=ethylene glycol dimethacrylate, the wt % of ethylene glycol directly impacted the tau0 of the formulation. An increase in ethylene glycol dimethacrylate changed the tau0 from 268 μs to 279 μs. With the same formulations, by keeping the wt % of Component 3=ethylene glycol constant at approximately 9.8, adding a Component 2=hydroxypropyl methacrylate increased the tau0 from 279 μs to 297 μs. These examples offer some direct comparisons of the ability to change components and ratios of the components to change the behavior of the polymer. Overall, changing components and ratios of the polymer while utilizing the same dye resulted in tau0 measurements from 101 μs to 411.6 μs.

Example 3-4-Plex Sensor

As discussed above, a luminescent sensing compound can be formulated with different polymers to produce different sensing compounds having different luminescent lifetimes, which can be deconvoluted to detect two different analytes. Example 2 illustrates a 4-plex sensor.

A first sensor portion can be composed of a first polymer matrix and a first $O_2$-sensitive luminescent dye, such as Pd-BP-AEME-4. A second sensor portion composed of a second polymer matrix and the first $O_2$-sensitive luminescent dye. A third sensor portion can be composed of the third polymer matrix and a second $O_2$-sensitive luminescent dye, such as QMAP. A fourth sensor portion can be composed of a fourth polymer matrix and the second $O_2$-sensitive luminescent dye. In some embodiments, the first polymer matrix can be the same or similar to the third polymer matrix, and/or the second polymer matrix can be the same or similar to the fourth polymer matrix. The first, sensor portion, the second sensor portion, the third sensor portion, and the fourth sensor portion can each be portions of a single sensor. Similarly stated, the sensor can be a single body having different dye-polymer portions configured to be implanted into a subject.

The formulations of the first sensor portion and the second sensor portion of multi-analyte sensor are selected to yield a long-lifetime signal and a short-lifetime signal from the first $O_2$-sensitive luminescent dye (e.g., Pd-BP-AEME-4) for monitoring a first analyte and a second analyte. Accordingly, multi-analyte sensor is capable of emitting, in response to a first excitation light, two analyte-dependent optical signals with the same emission wavelength, wherein the two analyte-dependent optical signals may be distinguished by their different lifetime characteristics.

The formulations of the third sensor portion and the fourth sensor portion of multi-analyte sensor are selected to yield a long-lifetime signal and a short-lifetime signal from the second $O_2$-sensitive luminescent dye for monitoring a third analyte and a fourth analyte. Accordingly, multi-analyte sensor is capable of emitting, in response to a second excitation light, two analyte-dependent optical signals with the same emission wavelength, wherein the two analyte-dependent optical signals may be distinguished by their different lifetime characteristics.

In one example, multi-analyte sensor is an $O_2$, glucose, lactate, and pyruvate sensor. For example, a first $O_2$-sensitive luminescent dye in the first sensor portion acts as a first sensing moiety for sensing $O_2$. The second sensor portion includes the first $O_2$-sensitive luminescent dye and a second sensing moiety, glucose oxidase, for detection of glucose. The third sensor portion includes a second $O_2$-sensitive luminescent dye and a third sensing moiety, lactate oxidase, for detection of lactate. The fourth sensor portion includes the second $O_2$-sensitive luminescent dye and a fourth sensing moiety, pyruvate oxidase, for detection of pyruvate.

In some embodiments, the first $O_2$-sensitive dye and the second $O_2$-sensitive dye can have different excitation wavelengths. Similarly stated, a reader can be configured to emit excitation light in two wavelengths, one wavelength to excite the first $O_2$-sensitive dye, and a second wavelength to excite the second $O_2$ sensitive dye. In some such embodiments, the first $O_2$-sensitive dye and the second $O_2$-sensitive dye can be excited simultaneously. Similarly, the reader can include one or more detectors operable to detect emission light across emission spectra for both the first $O_2$-sensitive dye and the second $O_2$-sensitive dye. In some such embodiments, the reader can be configured to detect emission signals emitted simultaneously from first $O_2$-sensitive dye and the second $O_2$-sensitive dye.

Figure 7A:
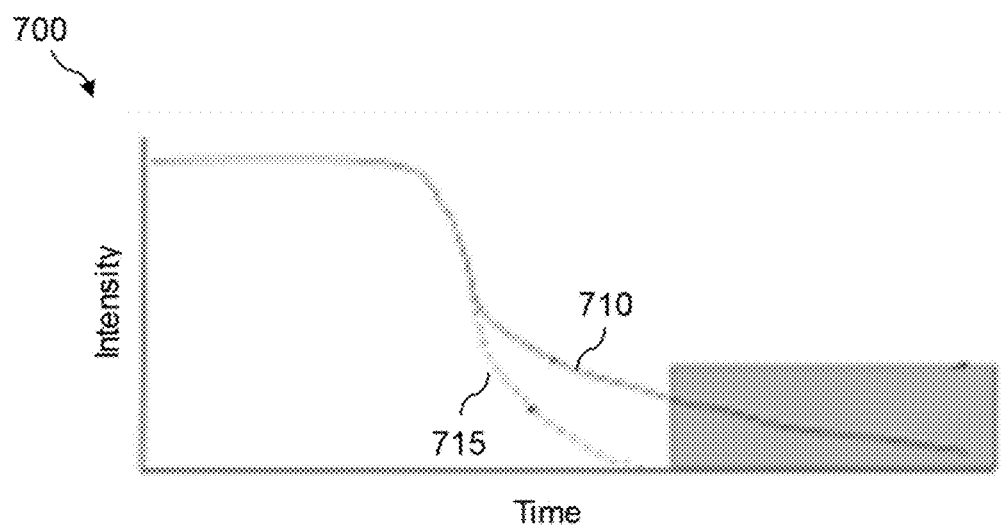
FIGS. 7A and 7B are plots of example the emission intensities of a multi-analyte sensor.

FIG. 7A is a plot 700 of an example of the emission intensity of the 4-plex multi-analyte sensor. Plot 700 indicates the combined short-lifetime and long-lifetime components of a first optical signal returned from multi-analyte sensor, and the deconvoluted short-lifetime component. Namely, a curve 710 indicates the emission intensity of the optical signal returned from multi-analyte sensor 110, wherein the optical signal includes emission from both the long-lifetime component (e.g., $O_2$ component) and the short-lifetime component (e.g., glucose component) of the sensor. A curve 715 indicates the emission intensity of the short-lifetime component deconvoluted from the combined optical signal (i.e., curve 710) returned from multi-analyte sensor 110. The area of curve 710 highlighted in gray represents the long-lifetime component of the sensor.

Figure 7B:
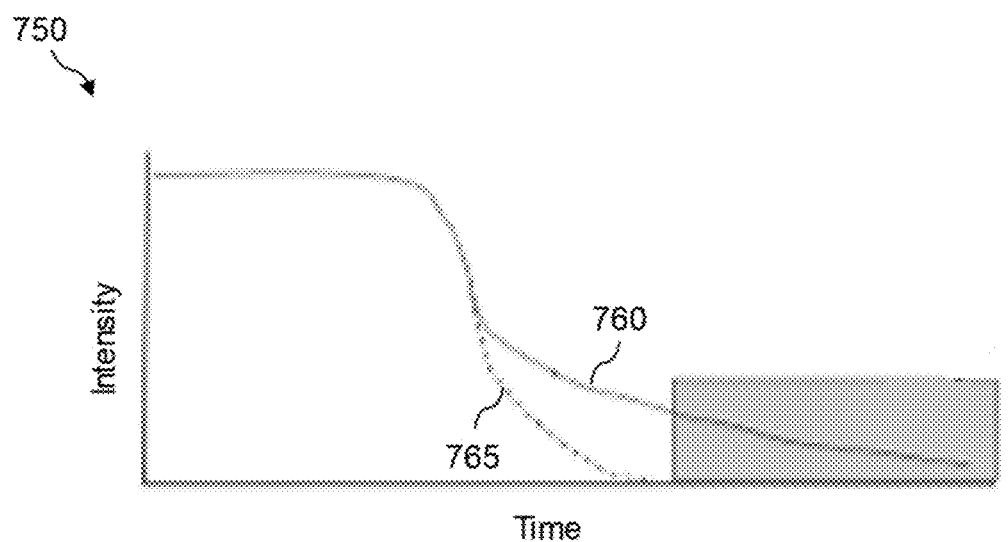

FIG. 7B is a plot 750 of an example of the emission intensity of the 4-plex multi-analyte sensor. Plot 750 indicates the combined short-lifetime and long-lifetime components of a second optical signal returned from multi-analyte sensor and the deconvoluted short-lifetime component. Namely, a curve 760 indicates the emission intensity of the optical signal returned from multi-analyte sensor 110, wherein the optical signal includes emission from both the long-lifetime component (e.g., pyruvate component) and the short-lifetime component (e.g., lactate component) of the sensor. A curve 765 indicates the emission intensity of the short-lifetime component deconvoluted from the combined optical signal (i.e., curve 760) returned from multi-analyte sensor 110. The area of curve 760 highlighted in gray represents the long-lifetime component of the sensor.

Example 4—9-Plex Sensor

Table 3 below shows an example of a design layout for multiplexing the simultaneous detection of nine analytes using three $O_2$-sensitive porphyrin dyes and three different polymers. Each porphyrin dye, P1, P2, and P3 can have a different excitation and/or emission spectra and can each be formulated with three different polymers, H1, H2, and H3, causing temporal shifts in characteristic emission for each of the dyes. Each dye-polymer combination is paired with an individual enzyme or other suitable analyte-reactive agent (except for the analysis of $O_2$) for the analysis of a specific analyte (e.g., alcohol, bilirubin, lactate, ascorbate, cholesterol, glucose, histamine, and pyruvate).

TABLE 3

Example 9-plex multi-analyte sensor

|    | P1       | P2          | P3        |
|----|----------|-------------|-----------|
| H1 | Oxygen   | Lactate     | Glucose   |
| H2 | Alcohol  | Ascorbate   | Histamine |
| H3 | Bilirubin| Cholesterol | Pyruvate  |

Further, using the 9-plex sensor design described with reference to Table 3 above, three "channels" may be dedicated to detecting a single analyte. Table 4 below shows an example of a design layout, wherein three "channels" are dedicated to detecting $O_2$ for improved accuracy for an $O_2$-based sensing platform.

TABLE 4

Example 9-plex sensor with dedicated O2 channels

|    | P1       | P2        | P3        |
|----|----------|-----------|-----------|
| H1 | Oxygen   | Lactate   | Glucose   |
| H2 | Alcohol  | Ascorbate | Histamine |
| H3 | Bilirubin| Oxygen    | Oxygen    |

Table 5 below shows another example of a design layout, wherein three channels are dedicated to detecting any three analytes for improved accuracy through repetition.

TABLE 5

Example 9-plex sensor with dedicated 3-analyte channels

|    | P1      | P2      | P3      |
|----|---------|---------|---------|
| H1 | Oxygen  | Lactate | Glucose |
| H2 | Glucose | Oxygen  | Lactate |
| H3 | Lactate | Glucose | Oxygen  |

Example 5—Dual Sensors

TABLE 6

| Formulation | Total Volume (uL) | Component 1/Component 2/Component 3 | Cosolvents | Dye | Enzymatic Components (w/v %) |
|---|---|---|---|---|---|
| Lactate Sensor | 500 | HEMA/HPMA/EGDMA (63.4/26.7/9.8% w/w of monomer and/or polymer content of major components) | 0.67M 1-Methyl-2-pyrrolidinone (NMP) | 1 mM Pd-BP-AEME-4 in NMP | 2.1% (w/v) LOx from *Aerococcus viridans* |
| Coating | 200 | 0.88 mM polycarbonate in methylene chloride | 15.7M Methylene chloride | NA | NA |

TABLE 6-continued

| Formulation | Total Volume (uL) | Component 1/Component 2/Component 3 | Cosolvents | Dye | Enzymatic Components (w/v %) |
|---|---|---|---|---|---|
| Oxygen Sensor | 230 | PUD640 (5% wt/v in 9:1 ethanol/water)/PEGDA700 (16.7/83.3% w/w of polymer content only) | 0.45M NMP | 1.3 mM Pd-BP-AEME -4 in NMP | NA |

Table 6 outlines the synthesis components of a dual sensor with a lactate sensor portion, passive layer (coating) and oxygen sensor portion. The first sensing layer, including lactate oxidase, of a layered lactate sensor was prepared as follows (Table 6): Irgacure 651 (Sigma-Aldrich), HEMA (Polysciences), HPMA (Sigma-Aldrich), EGDMA (Sigma-Aldrich), Pd-BMAP-AEME-4 (U.S. Pat. No. 9,375,494), and NMP (N-Methyl-2-pyrrolidone, Sigma-Aldrich) were added together and mixed well to form solution 1. 2-Aminoethylmethacrylate hydrochloride (AEMA, Sigma-Aldrich), LOx (Lactate Oxidase, Sekisui) from *Aerococcus viridans*, and PBS (phosphate buffered saline, 20 mM) were mixed together to form solution 2. Solution 1 was added to solution 2 to get a mixture with final concentrations of Irgacure 651 (19.5 mM), HEMA (3.63 M), HPMA (1.35 M), EGDMA (0.37 M), AEMA (0.56 mM), Pd-BMAP-AEMA-4 (1 mM), NMP (0.67 M) and enzymatic component (LOx, 2.1% wt/v) in 20 mM PBS such that the PBS volume was 18.8% of the total volume mixture. The mixture was polymerized and prepared for the coating process.

Application of a Coating to the First Sensing Layer

A coating was applied to the first sensing layer including lactate oxidase prepared above. Water on the surface of the lactate sensing layer was removed. The sensing layers were coated with a polycarbonate solution ((VWR) 0.88 mM in methylene chloride (Sigma-Aldrich)) and dried. After coating, the sensors were stored in PBS (20 mM) solution.

Additional passive layers were prepared as described above, using the tubings and coatings and combinations thereof shown in Table 7.

Application of a Second Sensing Layer

A second sensing layer, functioning as a reference, was applied to the coating on the first sensing layer prepared above.

Irgacure 651 (19.5 mM), PEGDA700 (poly(ethylene glycol) diacrylate average $M_n$ 700, 83.3% w/w of polymer content only, Sigma-Aldrich), Pd-BMAP-AEME-4 (1.3 mM, prepared as described above), NMP (0.45M), and PU D640 (5 wt/v % in ethanol/water 9:1 v/v, 16.7% w/w of polymer content only, AdvanSource Biomaterials Inc.) were mixed such that the ethanol/water solution was 72% (v/v) to form the oxygen reference layer (solution 3) solution. To incorporate the oxygen reference solution on the passive layer, the water on the surface of the passive layer was removed. The coating was then applied to the surface. Coated sensors were then stored in PBS.

Table 7 shows additional examples of lactate/O2 sensors and Table 8 shows additional examples of oxygen/oxygen sensors. Displayed in the table are the weight percentages of the major monomer and/or polymer components with respect to each other. For testing, lactate/oxygen and oxygen/oxygen sensors were placed in a customized test fixture with controllable oxygen levels. All sensors were tested in 500 mL of PBS and allowed to equilibrate at 37° C. An oxygen modulation was performed on the sensors. Automated gas mixing systems were used to modulate oxygen concentration at stepwise decreases in concentration. Sensors were tested at 0, 0.25, 0.5, 1, 2, 5, 10, 21% oxygen. At each oxygen concentration, the sensor phosphorescence signal was equilibrated and phosphorescent lifetimes from each sensing portion was calculated using custom algorithms. Response curves were generated by averaging the phosphorescence signal of the last 2 minutes of each step prior to changes in oxygen. The tau0 reported in Tables 7 and 8 refer to the calculated phosphorescent decay at 0% oxygen. Higher ratios (>1.6) between the two sensing layers are desirable for accurate temporal separation and measurements from each layer.

TABLE 7

| Component 1 | Component 2 | Component 3 | wt % cmpt 1 | wt % cmpt 2 | wt % cmpt 3 | Dye or Sensor | tau0 (us) | Ratio of tau0 for Lactate Sensing Layer/Oxygen Sensing Layer |
|---|---|---|---|---|---|---|---|---|
| 2-hydroxyethyl methacrylate | hydroxypropyl methacrylate | ethylene glycol dimethacrylate | 63.42 | 26.73 | 9.86 | Pd-BP-AEME-4 | 307.88 | 2.26 |
| Polyurethane D640 (5%) | poly(ethylene glycol) diacrylate | | 16.71 | 83.29 | | Pd-BP-AEME-1 | 136.09 | |
| 2-hydroxyethyl methacrylate | hydroxypropyl methacrylate | ethylene glycol dimethacrylate | 63.42 | 26.73 | 9.86 | Pd-BP-AEME-4 | 278.41 | 1.75 |
| Polyurethane D640 (5%) | poly(ethylene glycol) diacrylate | | 16.71 | 83.29 | | Pd-BP-AEME-4 | 158.68 | |
| 2-hydroxyethyl methacrylate | hydroxypropyl methacrylate | ethylene glycol dimethacrylate | 63.42 | 26.73 | 9.86 | Pd-BP-AEME-4 | 309.58 | 1.86 |
| Polyurethane D640 (5%) | poly(ethylene glycol) diacrylate | | 16.71 | 83.29 | | Pd-BP-AEME-4 | 166.76 | |

TABLE 7-continued

| Component 1 | Component 2 | Component 3 | wt % cmpt 1 | wt % cmpt 2 | wt % cmpt 3 | Dye or Sensor | tau0 (us) | Ratio of tau0 for Lactate Sensing Layer/Oxygen Sensing Layer |
|---|---|---|---|---|---|---|---|---|
| 2-hydroxyethyl methacrylate | hydroxypropyl methacrylate | ethylene glycol dimethacrylate | 63.42 | 26.73 | 9.86 | Pd-BP-AEME-4 | 325.15 | 1.82 |
| Polyurethane D640 (5%) | poly(ethylene glycol) diacrylate | | 16.71 | 83.29 | | Pd-BP-AEME-4 | 178.37 | |
| 2-hydroxyethyl methacrylate | hydroxypropyl methacrylate | ethylene glycol dimethacrylate | 63.42 | 26.73 | 9.86 | Pd-BP-AEME-4 | 276.67 | 1.86 |
| Polyurethane D640 (5%) | poly(ethylene glycol) diacrylate | | 16.71 | 83.29 | | Pd-BP-AEME-4 | 149.10 | |
| 2-hydroxyethyl methacrylate | hydroxypropyl methacrylate | ethylene glycol dimethacrylate | 63.42 | 26.73 | 9.86 | Pd-BP-AEME-4 | 306.88 | 1.94 |
| Polyurethane D640 (5%) | poly(ethylene glycol) diacrylate | | 16.71 | 83.29 | | Pd-BP-AEME-4 | 158.49 | |
| 2-hydroxyethyl methacrylate | hydroxypropyl methacrylate | ethylene glycol dimethacrylate | 63.42 | 26.73 | 9.86 | Pd-BP-AEME-4 | 294.50 | 2.12 |
| Polyurethane D640 (5%) | poly(ethylene glycol) diacrylate | | 16.71 | 83.29 | | Pd-BP-AEME-4 | 138.72 | |
| 2-hydroxyethyl methacrylate | hydroxypropyl methacrylate | ethylene glycol dimethacrylate | 63.42 | 26.73 | 9.86 | Pd-BP-AEME-4 | 321.63 | 1.73 |
| Polyurethane D640 (5%) | poly(ethylene glycol) diacrylate | | 16.71 | 83.29 | | Pd-BP-AEME-4 | 185.55 | |
| 2-hydroxyethyl methacrylate | hydroxypropyl methacrylate | ethylene glycol dimethacrylate | 63.42 | 26.73 | 9.86 | Pd-BP-AEME-4 | 325.58 | 1.80 |
| Polyurethane D640 (5%) | poly(ethylene glycol) diacrylate | | 16.71 | 83.29 | | Pd-BP-AEME-4 | 180.72 | |
| 2-hydroxyethyl methacrylate | hydroxypropyl methacrylate | ethylene glycol dimethacrylate | 63.42 | 26.73 | 9.86 | Pd-BP-AEME-4 | 278.95 | 1.71 |
| Polyurethane D640 (5%) | poly(ethylene glycol) diacrylate | | 21.13 | | 78.87 | Pd-BP-AEME-4 | 163.01 | |
| 2-hydroxyethyl methacrylate | hydroxypropyl methacrylate | ethylene glycol dimethacrylate | 63.42 | 26.73 | 9.86 | Pd-BP-AEME-4 | 308.79 | 1.68 |
| Polyurethane D640 (5%) | poly(ethylene glycol) diacrylate | | 21.13 | 78.87 | | Pd-BP-AEME-4 | 183.47 | |

TABLE 8

| Component 1 | Component 2 | Component 3 | wt % cmpt 1 | wt % cmpt 2 | wt % cmpt 3 | Dye or Sensor | tau0 (us) | Ratio of tau0 for Layer 1/Layer 2 |
|---|---|---|---|---|---|---|---|---|
| 2-hydroxyethyl methacrylate | hydroxypropyl methacrylate | ethylene glycol dimethacrylate | 63.42 | 26.73 | 9.86 | Pd-BP-AEME-4 | 304.08 | 2.32 |
| Polyurethane D640 (5%) | poly(ethylene glycol) diacrylate | | 16.71 | 83.29 | | Pd-BP-AEME-1 | 130.93 | |
| 2-hydroxyethyl methacrylate | hydroxypropyl methacrylate | ethylene glycol dimethacrylate | 63.42 | 26.73 | 9.86 | Pd-BP-AEME-4 | 311.98 | 1.66 |
| Polyurethane D640 (5%) | poly(ethylene glycol) diacrylate | | 16.71 | 83.29 | | Pd-BP-AEME-4 | 187.76 | |
| 2-hydroxyethyl methacrylate | hydroxypropyl methacrylate | ethylene glycol dimethacrylate | 63.42 | 26.73 | 9.86 | Pd-BP-AEME-4 | 313.13 | 1.83 |
| Polyurethane D640 (5%) | poly(ethylene glycol) diacrylate | | 16.71 | 83.29 | | Pd-BP-AEME-4 | 171.33 | |
| 2-hydroxyethyl methacrylate | hydroxypropyl methacrylate | ethylene glycol dimethacrylate | 63.42 | 26.73 | 9.86 | Pd-BP-AEME-4 | 315.64 | 1.81 |
| Polyurethane D640 (5%) | poly(ethylene glycol) diacrylate | | 16.71 | 83.29 | | Pd-BP-AEME-4 | 174.61 | |
| 2-hydroxyethyl methacrylate | hydroxypropyl methacrylate | ethylene glycol dimethacrylate | 63.42 | 26.73 | 9.86 | Pd-BP-AEME-4 | 282.33 | 1.89 |
| Polyurethane D640 (5%) | poly(ethylene glycol) diacrylate | | 16.71 | 83.29 | | Pd-BP-AEME-4 | 149.26 | |

TABLE 8-continued

| Component 1 | Component 2 | Component 3 | wt % cmpt 1 | wt % cmpt 2 | wt % cmpt 3 | Dye or Sensor | tau0 (us) | Ratio of tau0 for Layer 1/Layer 2 |
|---|---|---|---|---|---|---|---|---|
| 2-hydroxyethyl methacrylate | hydroxypropyl methacrylate | ethylene glycol dimethacrylate | 63.42 | 26.73 | 9.86 | Pd-BP-AEME-4 | 316.04 | 1.96 |
| Polyurethane D640 (5%) | poly(ethylene glycol) diacrylate | | 16.71 | 83.29 | | Pd-BP-AEME-4 | 161.02 | |
| 2-hydroxyethyl methacrylate | hydroxypropyl methacrylate | ethylene glycol dimethacrylate | 63.42 | 26.73 | 9.86 | Pd-BP-AEME-4 | 295.42 | 2.27 |
| Polyurethane D640 (5%) | poly(ethylene glycol) diacrylate | | 16.71 | 83.29 | | Pd-BP-AEME-4 | 130.13 | |
| 2-hydroxyethyl methacrylate | hydroxypropyl methacrylate | ethylene glycol dimethacrylate | 63.42 | 26.73 | 9.86 | Pd-BP-AEME-4 | 328.34 | 1.74 |
| Polyurethane D640 (5%) | poly(ethylene glycol) diacrylate | | 16.71 | 83.29 | | Pd-BP-AEME-4 | 188.27 | |
| 2-hydroxyethyl methacrylate | hydroxypropyl methacrylate | ethylene glycol dimethacrylate | 63.42 | 26.73 | 9.86 | Pd-BP-AEME-4 | 330.33 | 1.75 |
| Polyurethane D640 (5%) | poly(ethylene glycol) diacrylate | | 16.71 | 83.29 | | Pd-BP-AEME-4 | 188.33 | |
| 2-hydroxyethyl methacrylate | hydroxypropyl methacrylate | ethylene glycol dimethacrylate | 63.42 | 26.73 | 9.86 | Pd-BP-AEME-4 | 334.30 | 1.64 |
| Polyurethane D640 (5%) | poly(ethylene glycol) diacrylate | | 21.13 | 78.87 | | Pd-BP-AEME-4 | 204.31 | |
| 2-hydroxyethyl methacrylate | hydroxypropyl methacrylate | ethylene glycol dimethacrylate | 63.42 | 26.73 | 9.86 | Pd-BP-AEME-4 | 308.35 | 1.69 |
| Polyurethane D640 (5%) | poly(ethylene glycol) diacrylate | | 21.13 | 78.87 | | Pd-BP-AEME-4 | 182.42 | |

Example 6—Particle Sensors

Particles with dye were synthesized by mixing the components listed in Table 9. The components were added to a beaker and the mixture was sonicated on ice for 10 minutes. The solution was then covered with aluminum foil and deoxygenated with argon for at least 10 minutes. The beaker was covered with Saran wrap, placed on a stir plate directly under a UV lamp. The mixture was left to stir for 2.5 hours under UV exposure. After 2.5 hours, unreacted reagents and surfactants were removed by adding 1 N HCl until the pH was approximately 3. Acetone was added to take 70% of the total volume and the mixture was centrifuged for 15 minutes at approximately 6500 rpm. Supernatant was removed and pellet was resuspended in 5 mL of 0.5 N HCl. The removal of supernatant was repeated for a total of 5 times. After the last wash, the particles were either dried or resuspended in water and stored away from light.

Particles from Table 9 were incorporated into a polymer of Component 1=hydroxyethyl methacrylate (98%) and Component 2=tetra(ethylene glycol) dimethacrylate (2%). The host polymer did not contain any dye itself and that volume was replaced with dimethyl sulfoxide. The particles were incorporated at an amount between 5 to 25 mg particles per 100 μL of pre-polymer solution of Component 1, Component 2, initiator, and co-solvents. At the bottom of Table 9 are the results after incorporation Particles 1, 2, and 3 into the host polymer. The incorporation of particles synthesized with different polymer components and ratios resulted in tau0 varying from 281 to 322 μs.

TABLE 9

| | Amount |
|---|---|
| Particle 1 | |
| Polyethylene glycol methyl ether methacrylate (50% wt in water) | 250 μL |
| DI Water | 2.25 mL |
| 2,2-Dimethoxy-2-phenylacetonphenone | 1.283 mg |
| 2-(Diethylamino)ethyl methacrylate | 135.5 μL |
| Butyl methacrylate | 21.5 μL |
| tetra(ethylene glycol) dimethacrylate | 38 μL |
| Myristyltrimethylammonium bromide | 2.86 mg |
| Dodecyl tetraethylene glycol ether | 10 μL |
| Pd-BP-AEME-4 (10 mM in DMSO) | 32 μL |
| Particle 2 | |
| Hydroxyethyl methacrylate | 125 μL |
| DI Water | 2.375 mL |
| 2,2-Dimethoxy-2-phenylacetonphenone | 1.283 mg |
| Aminoethyl methacrylate | 135.5 μL |
| Butyl methacrylate | 21.5 μL |
| tetra(ethylene glycol) dimethacrylate | 38 μL |
| Myristyltrimethylammonium bromide | 2.86 mg |
| Dodecyl tetraethylene glycol ether | 10 μL |
| Pd-BP-AEME-4 (10 mM in DMSO) | 32 μL |
| Particle 3 | |
| Hydroxyethyl methacrylate | 260.5 μL |
| DI Water | 2.375 mL |
| 2,2-Dimethoxy-2-phenylacetonphenone | 1.283 mg |
| Butyl methacrylate | 21.5 μL |
| tetra(ethylene glycol) dimethacrylate | 38 μL |
| Myristyltrimethylammonium bromide | 2.86 mg |
| Dodecyl tetraethylene glycol ether | 10 μL |
| Pd-BP-AEME-4 (10 mM in DMSO) | 32 μL |

TABLE 9-continued

| Particle | Particle concentration | Tau0 (µs) |
|---|---|---|
| Particle 1 | 25 (mg/100 µL) | 280.9 |
| Particle 2 | 25 (mg/100 µL) | 321.5 |
| Particle 3 | 12.5 (mg/100 µL) | 295.1 |

Figure 8:
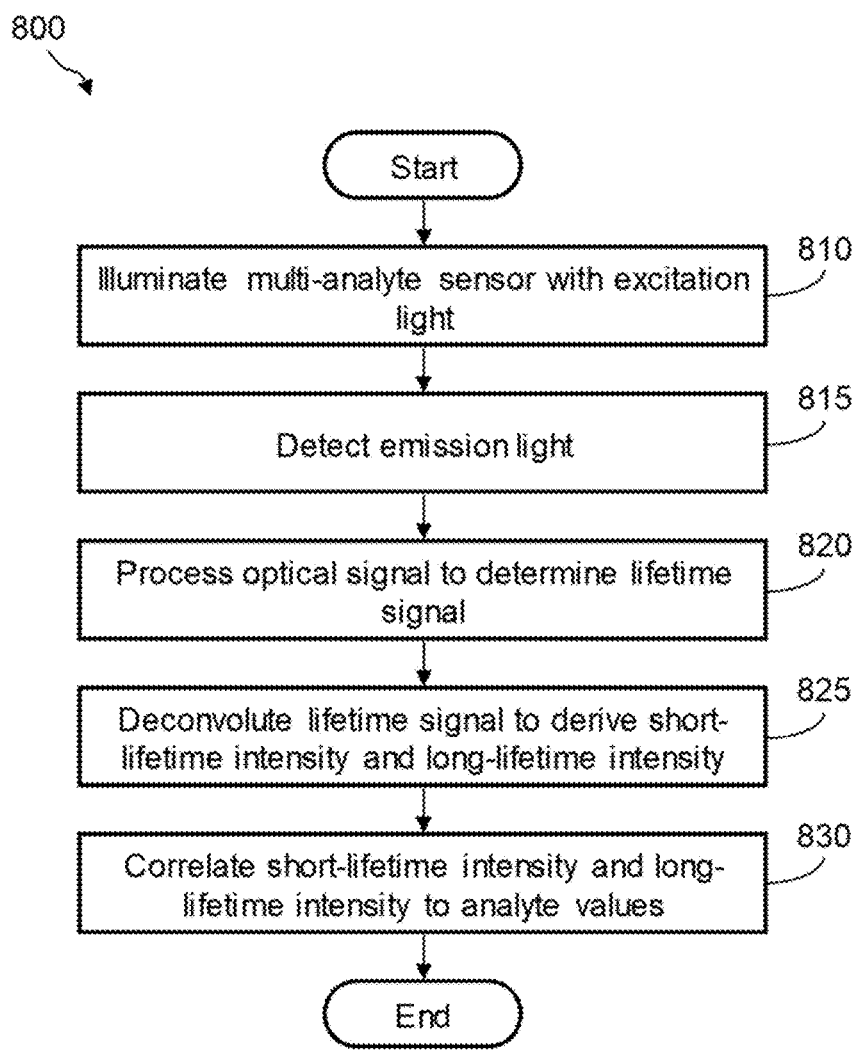
FIG. 8, a flow diagram of method of detecting one or more analytes, according to an embodiment.
Figure 9:
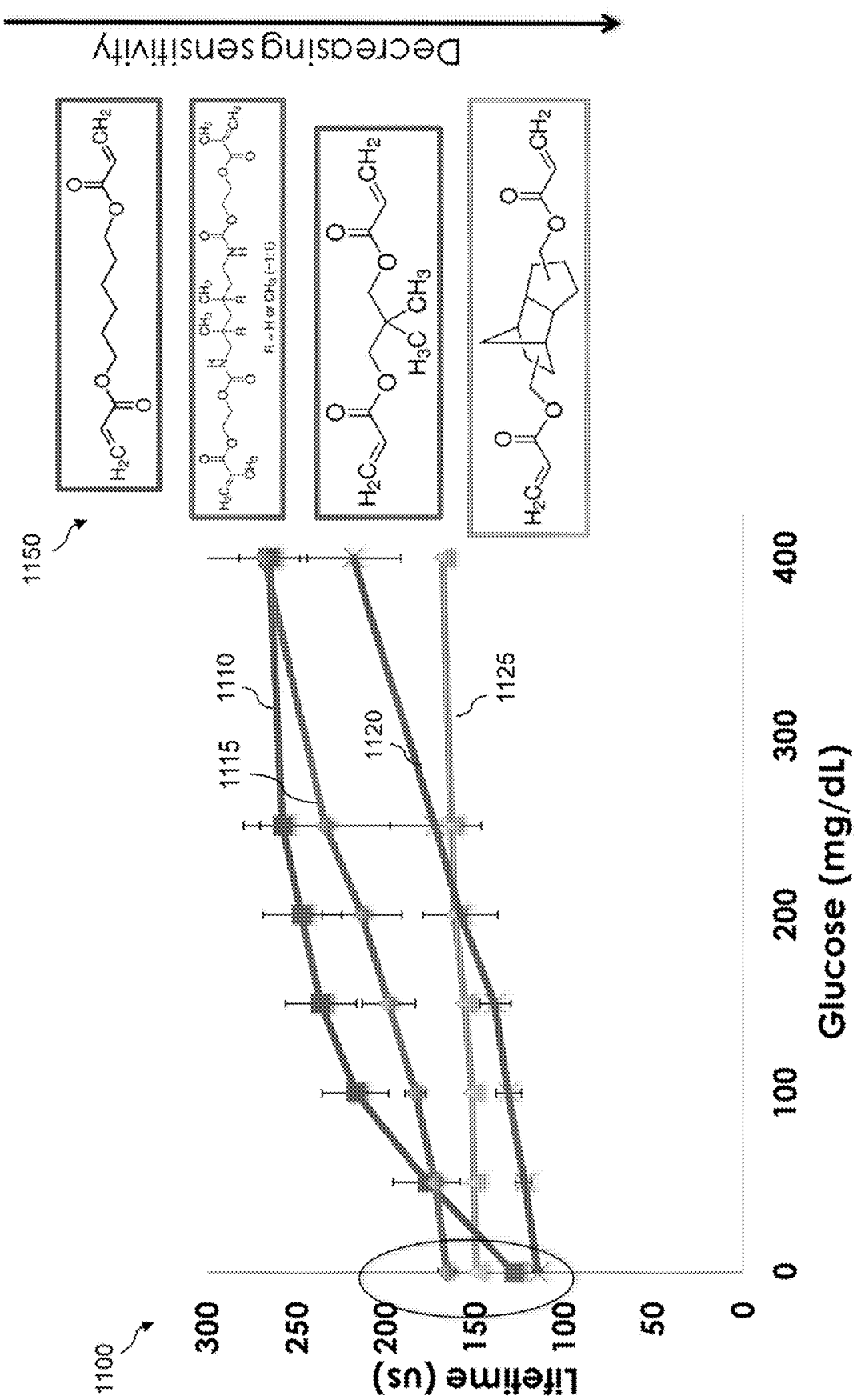
FIG. 9 is a plot of an example of the effect of different sensor crosslinker components have on the detection sensitivity of a sensor.

Reference is now made to FIG. 8, a flow diagram of method 800 of detecting one or more analytes. For example, the method 800 can be implemented using the system 100 as shown and described with reference to FIG. 5 and/or any of the sensors and/or dye-polymer formulations described herein to determine an analyte value (e.g., analyte quantity and/or concentration). For ease of description, method 800 is described with reference to system 100 as measuring a glucose and an $O_2$ concentration using a multi-analyte sensor 110 having a first sensing portion that includes an $O_2$ sensitive luminescent sensing compound and a second sensing portion that includes the same $O_2$ sensing compound and glucose oxidase.

At a step 810, optical detector 115 is placed on the skin in close proximity to sensor 110. Then, sensor 110 is illuminated by pulsing light source 120.

At a step 815, emission light 142 from first sensing portion and the second sensing portion of sensor 110 is captured via detector 125. Because first sensor portion and second sensor portion are composed of different polymer matrices, emission light 142 from sensor 110 includes a long-lifetime component and a short-lifetime component.

At a step 820, the optical signal captured by detector 125 is processed to determine a lifetime signal that is a mix of long-lifetime and short-lifetime components. An example of a combined lifetime signal is shown in plot 400 of FIG. 6.

At a step 825, the lifetime signal determined in step 820 is deconvoluted to derive the short-lifetime intensity and the long-lifetime intensity. The short-lifetime signal corresponds to the optical signal from second sensor portion (e.g., the glucose sensor portion) and the long-lifetime corresponds to the optical signal from first sensor portion (e.g., the $O_2$ sensor portion). An example of a deconvoluted lifetime signal is shown in plot 400 of FIG. 6.

At a step 830, the short-lifetime intensity and the long-lifetime intensity are correlated to analyte values (e.g., analyte quantity and/or concentrations).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range.

Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims. While various embodiments have been described herein, it should be understood that they have been presented by way of example only, and not limitation. Furthermore, although various embodiments have been described as having particular features and/or combinations of components, other embodiments are possible having a combination of any features and/or components from any of embodiments where appropriate as well as additional features and/or components.

Where methods described herein indicate certain events occurring in certain order, the ordering of certain events may be modified. Additionally, certain of the events may be performed repeatedly, concurrently in a parallel process when possible, as well as performed sequentially as described above. Furthermore, certain embodiments may omit one or more described events. Where methods are described, it should be understood that such methods can be computer-implemented methods. Similarly stated, a non-transitory processor readable medium can store code representing instructions configured to cause a processor to cause the described method to occur or be carried out.

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. A sensor, comprising:
   a first polymer-luminescent sensing compound configured to produce a first luminescent signal in the presence of a first analyte; and
   a second polymer-luminescent sensing compound configured to produce a second luminescent signal in the presence of a second analyte, the second luminescent signal having a luminescent lifetime that is at least 1.1 times greater than a luminescent lifetime of the first luminescent signal, the first luminescent signal and the second luminescent signal having a common spectral signature.

2. The sensor of claim 1, wherein the second polymer-luminescent sensing compound has a luminescent lifetime that is at least 1.6 times greater than the luminescent lifetime of the first polymer-luminescent sensing compound.

3. The sensor of claim 1, wherein the luminescent lifetime of the second polymer-luminescent sensing compound exceeds 350 microseconds.

4. The sensor of claim 1, wherein the second polymer-luminescent sensing compound includes:
   Pd-BP-AEME-4,
   hydroxyethyl methacrylate, and
   ethylene glycol dimethacrylate, a weight percentage of ethylene glycol dimethacrylate selected such that the second luminescent signal has the luminescent lifetime that is at least 1.1 times greater than a luminescent lifetime of the first luminescent signal.

5. The sensor of claim 1, wherein the first analyte is oxygen and the second analyte is glucose.

6. The sensor of claim 1, wherein:
   the first polymer-luminescent sensing compound includes an oxygen-sensitive dye;
   the second polymer-luminescent sensing compound includes the oxygen-sensitive dye;
   the first analyte is oxygen; and
   the second analyte is selected from the group consisting of glucose, lactate, alcohol, ascorbate, histamine, cholesterol, and pyruvate.

7. The sensor of claim 6, wherein the second polymer-luminescent sensing compound includes an oxidase configured to cause oxygen to form $H_2O_2$ in the presence of the second analyte such that the oxygen-sensitive dye included in the second polymer-luminescent sensing compound produces the second luminescent signal based on a concentration of the second analyte.

8. A sensor, comprising:
   a first polymer-luminescent sensing compound configured to produce a first luminescent signal in the presence of a first analyte; and
   a second polymer-luminescent sensing compound configured to produce a second luminescent signal in the presence of a second analyte, the second polymer-luminescent sensing compound including a luminescent sensing compound and a polymer, the polymer configured to alter a characteristic of the luminescent sensing compound such that the second luminescent signal is distinguishable from the first luminescent signal.

9. The sensor of claim 8, wherein the first polymer-luminescent sensing compound includes the luminescent sensing compound.

10. The sensor of claim 8, wherein the luminescent sensing compound is a first luminescent sensing compound, the first polymer-luminescent sensing compound including a second luminescent sensing compound.

11. The sensor of claim 8, wherein the second polymer is configured to increase an intensity of the luminescent sensing compound such that the second luminescent signal has an intensity within 25% of an intensity of the first luminescent signal.

12. The sensor of claim 8, wherein the second polymer is configured to alter a lifetime of the luminescent sensing compound such that the second luminescent signal has a lifetime at least 1.1 times a lifetime of the first luminescent signal.

13. The sensor of claim 12, wherein the first polymer-luminescent sensing compound includes the luminescent sensing compound.

14. The sensor of claim 8, wherein the luminescent sensing compound and the polymer are chemically bound to form the second polymer-luminescent sensing compound.

15. The sensor of claim 8, wherein the luminescent sensing compound is physically bound to the polymer to form the second polymer-luminescent sensing compound.

16. A method, comprising:
   illuminating a sensor having a first polymer-luminescent sensing compound and a second polymer luminescent sensing compound with an excitation light;
   receiving, from the sensor, a luminescent signal including a component from the first polymer-luminescent sensing compound and a component from the second polymer luminescent sensing compound;
   deconvoluting the component from the first polymer-luminescent sensing compound and the component from the second polymer luminescent sensing compound based on the first polymer-luminescent sensing compound having a luminescent lifetime greater than a luminescent lifetime of the second polymer-luminescent sensing compound;
   determining a concentration of the first analyte based on the component of the emission spectrum associated with first polymer-luminescent sensing compound; and
   determining a concentration of the second analyte based on the component of the emission spectrum associated with second polymer-luminescent sensing compound.

17. The method of claim 16, wherein the component from the first polymer-luminescent sensing compound and the component from the second polymer luminescent sensing compound have the same emission spectrum.

18. The method of claim 16, wherein the first polymer-luminescent sensing compound has a luminescent lifetime at least 1.1 times greater than a luminescent lifetime of the second polymer-luminescent sensing compound.

* * * * *